United States Patent
Eckard et al.

(10) Patent No.: US 11,492,642 B2
(45) Date of Patent: Nov. 8, 2022

(54) **RESTORER FACTOR FOR THE *BACCATUM* CYTOPLASMIC MALE STERILITY SYSTEM IN PEPPER**

(71) Applicant: SEMINIS VEGETABLE SEEDS, INC., St. Louis, MO (US)

(72) Inventors: Jonathan T. Eckard, St. Louis, MO (US); Rebeca N. Schauland, St. Louis, MO (US); Dick Vreugdenhil, 's-Gravenzande (NL)

(73) Assignee: SEMINIS VEGETABLE SEEDS, INC, St. Louis, MO (US)

( * ) Notice: Subject to any disclaimer, the term of this patent is extended or adjusted under 35 U.S.C. 154(b) by 68 days.

(21) Appl. No.: 16/453,757

(22) Filed: Jun. 26, 2019

(65) Prior Publication Data

US 2020/0040357 A1    Feb. 6, 2020

Related U.S. Application Data

(60) Provisional application No. 62/690,728, filed on Jun. 27, 2018.

(51) Int. Cl.
*C12N 15/82* (2006.01)
*A01H 5/08* (2018.01)

(52) U.S. Cl.
CPC .......... *C12N 15/8287* (2013.01); *A01H 5/08* (2013.01)

(58) Field of Classification Search
CPC ................................................... A01H 6/822
See application file for complete search history.

(56) References Cited

U.S. PATENT DOCUMENTS

| | | |
|---|---|---|
| 5,866,764 A | 2/1999 | Gabor et al. |
| 6,096,944 A | 8/2000 | Vierling et al. |
| 6,207,367 B1 | 3/2001 | Helentjaris et al. |
| 6,414,226 B1 | 7/2002 | Hoogstraten |
| 6,639,132 B1 | 10/2003 | Duvick et al. |
| 9,642,318 B2 | 5/2017 | Gorguet et al. |
| 2017/0188535 A1 | 7/2017 | Gorguet et al. |
| 2018/0171353 A1 | 6/2018 | Eckhard et al. |
| 2020/0015446 A1 | 1/2020 | Eckard et al. |

FOREIGN PATENT DOCUMENTS

WO    1991/002069 A1    2/1991

OTHER PUBLICATIONS

Swamy. B.N. et al., Scientia Horticulturae (2017) vol. 222. pp. 175-179. (Year: 2017).*
Jo, Y.D. et al., Theor Appl Genet (2016) vol. 129, pp. 2003-2017. (Year: 2016).*
Jo et al. (Theor Appl Genet 129:2003-2017, 2016. (Year: 2016).*
U.S. Appl. No. 16/453,748, filed Jun. 26, 2019, Eckard, et al.
Berke, "Hybrid Seed Production in Capsicum", Journal of New Seeds, (2000), 49-67, 1(3-4).
Dhaliwal and Jindal, "Induction and Exploitation of Nuclear and Cytoplasmic Male Sterility in Pepper (*Capsicum* spp.): a Review," Journal of Horticultural Science & Biotechnology, (2014), 471-479, 89(5).
Ishikawa, et al., "High β-carotene and Capsaicinoid Contents in Seedless Fruits of 'Shishitoh' Pepper," HortScience: a publication of the American Society for Horticultural Science, (2004), 153-155, 39(1).
Kumar, et al., "Genetics and Distribution of Fertility Restoration Associated RAPD Markers in Inbreds of Pepper (*Capsicum annuum* L.)," Scientia Horticulturae, (2007), 197-202, 111(3).
Monteiro, et al., "Reproductive Characterization of Interspecific Hybrids Among Capsicum Species," Crop Breeding and Applied Biotechnology, (2011), 241-249, 11 (3).
Mulyantoro, et al., "Conversion of the Genic Male Sterility (GMS) System of Bell Pepper (*Capsicum annuum* L.) to Cytoplasmic Male Sterility (CMS)," Plant Breeding, (2014), 291-297, 133(2).
Shifriss, "Male Sterility in Pepper (*Capsicum annuum* L.)," Euphytica, (1997), 83-88, 93(1).
Tiwari, et al., "Selection of Sweet Pepper (*Capsicum annuum* L.) Genotypes for Parthenocarpic Fruit Growth," Acta Hort. 761, ISHS, (2007), 135-140.
Invitation to Pay Additional Fees regarding PCT Application No. PCT/US2019/039178, dated Sep. 18, 2019, 4 pages.
Invitation to Pay Additional Fees regarding PCT Application No. PCT/US2019/039185, dated Sep. 18, 2019, 3 pages.
Manzur et al., "Successful Wide Hybridization and Introgression Breeding in a Diverse Set of Common Peppers (*Capsicum annum*) Using Different Cultivated Aji (*C. baccatum*) Accessions as Donor Parents," PLOS One, 10(12):1-18, Dec. 7, 2015.
Lin et al.,"Restorer breeding in sweet pepper: Introgressing Rf allele from hot pepper through marker-assisted backcrossing," Scienta Horticulturae, vol. 197, pp. 170-175, Dec. 14, 2015.
Jo et al., "Development and evaluation of broadly applicable markers for Restorer-of-fertility in pepper," Molecular Breeding, 25(2):187-201, 2010.
International Search Report and Written Opinion regarding PCT Application No. PCT/US2019/039185, dated Nov. 26, 2019.
International Search Report and Written Opinion regarding PCT Application No. PCT/US2019/039178, dated Dec. 2, 2019.
GenBank Accession No. AC211024, Sep. 26, 2007.
GenBank Accession No. JW144115, Sep. 1, 2007.
GenBank Accession No. HG975443, Nov. 19, 2015.
USPTO: Response to Non-Final Office Action regarding U.S. Appl. No. 16/453,748, filed Jul. 12, 2021.
USPTO: Restriction Requirement regarding U.S. Appl. No. 16/453,748, dated Dec. 1, 2020.

(Continued)

*Primary Examiner* — Russell Kallis
(74) *Attorney, Agent, or Firm* — Dentons US LLP; Matthew L. Madsen

(57) ABSTRACT

The present disclosure provides *Capsicum annuum* BCMS plants comprising a male fertility restoration locus. Such plants comprise novel introgressed genomic regions associated with male fertility from *Capsicum annuum* on chromosome 6. In certain aspects, compositions and methods for producing, breeding, identifying, and selecting plants or germplasm with a male fertility phenotype are provided.

18 Claims, 3 Drawing Sheets

Specification includes a Sequence Listing.

(56) References Cited

OTHER PUBLICATIONS

USPTO: Response to Restriction Requirement regarding U.S. Appl. No. 16/453,748, filed Dec. 14, 2020.
USPTO: Non-Final Office Action regarding U.S. Appl. No. 16/453,748, dated Apr. 14, 2021.
USPTO: Response to Final Office Action regarding U.S. Appl. No. 16/453,748, filed Jan. 7, 2022.
USPTO: Notice of Allowance regarding U.S. Appl. No. 16/453,748, dated Feb. 8, 2022.
USPTO: Notice of Withdrawal from Issue under 37 CFR 1.313(b) regarding U.S. Appl. No. 16/453,748, dated Feb. 22, 2022.
USPTO: Examiner-Initiated Interview Summary regarding U.S. Appl. No. 16/453,748, dated Feb. 22, 2022.
USPTO: Non-Final Office Action regarding U.S. Appl. No. 16/453,748, dated Mar. 22, 2022.
USPTO: Final Office Action regarding U.S. Appl. No. 16/453,748, dated Oct. 13, 2021.
USPTO: Response to Non-Final Office Action regarding U.S. Appl. No. 16/453,748, filed Jun. 29, 2022.
USPTO: Notice of Allowance regarding U.S. Appl. No. 16/453,748, dated Jul. 21, 2022.

\* cited by examiner

FIG. 1

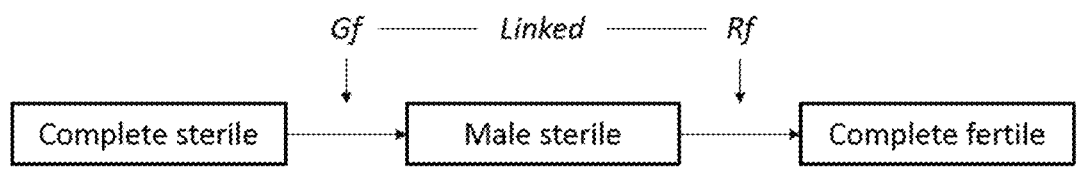

*gfRf* = annuum restoration haplotype    *gfrf* = annuum non-restoration haplotype
*Gfrf* = baccatum haplotype

| Possible genotypes | Female fertility | Male fertility | Flower class |
|---|---|---|---|
| *Gfrf/Gfrf* | Fertile | Sterile | Male sterile |
| *Gfrf/gfrf* | Fertile | Sterile | Male sterile |
| *Gfrf/gfRf* | Fertile | Fertile | Complete fertile |
| *gfrf/gfrf* | Sterile | Sterile | Complete sterile |
| *gfrf/gfRf* | Sterile | Sterile | Complete sterile |
| *gfRf/gfRf* | Sterile | Sterile | Complete sterile |

FIG. 3

Parental cross: BCMS Donor Line 1: (S)*Gfrf/gfrf* x 'Flame Fountain' (N)*gfRf/gfRf*

→ F$_1$: ½(S)*Gfrf/gfRf* (completely fertile) + ½(S)*gfrf/gfRf* (completely sterile)

→ F$_2$: ½(S)*Gfrf/gfRf* (completely fertile) + ½(S)*Gfrf/Gfrf* (male sterile)

→ ...

→ F$_n$: ½(S)*Gfrf/gfRf* (completely fertile) + ½(S)*Gfrf/Gfrf* (male sterile)

* note that (S)*Gfrf/Gfrf* plants cannot be selfed and do not contribute to next selfing generation.

RESTORER FACTOR FOR THE *BACCATUM* CYTOPLASMIC MALE STERILITY SYSTEM IN PEPPER

CROSS-REFERENCE TO RELATED APPLICATIONS

This application claims the benefit of priority of U.S. Provisional Appl. Ser. No. 62/690,728, filed Jun. 27, 2018, the disclosure of which is hereby incorporated by reference in its entirety.

INCORPORATION OF SEQUENCE LISTING

The sequence listing that is contained in the file named "SEMB035US-revised ST25.txt", which is 50.8 kilobytes as measured in Microsoft Windows operating system and was created on Aug. 10, 2022, is filed electronically herewith and incorporated herein by reference.

FIELD OF THE INVENTION

The present invention relates to the field of agriculture and more specifically to methods and compositions for producing pepper plants exhibiting restored male fertility.

BACKGROUND OF THE INVENTION

The goal of vegetable breeding is to combine various desirable traits in a single variety/hybrid. Production of hybrid peppers may be carried out by hand-emasculation or by using male sterility. A number of male sterility systems have been identified for use in pepper production, however each system has limitations. Efforts to overcome these limitations are hindered by a lack of specific markers linked to the alleles associated with male sterility phenotypes. The use of marker-assisted selection (MAS) in plant breeding methods has made it possible to select plants based on genetic markers linked to traits of interest. However, accurate markers for identifying or tracking desirable traits in plants are frequently unavailable even if a gene associated with the trait has been characterized. These difficulties are further complicated by factors such as polygenic or quantitative inheritance, epistasis and an often incomplete understanding of the genetic background underlying expression of a desired phenotype.

SUMMARY OF THE INVENTION

In one aspect, the present invention provides a *Capsicum annuum* plant comprising a *Capsicum baccatum* cytoplasm and comprising a chromosomal segment on chromosome 6 that confers male fertility in a male sterile *Capsicum annuum* plant comprising a *Capsicum baccatum* cytoplasm relative to a plant lacking said chromosomal segment. In some embodiments, the chromosomal segment is flanked by Marker M29 (SEQ ID NO: 29) and a marker selected from the group consisting of Marker M14 (SEQ ID NO: 14), Marker M15 (SEQ ID NO: 15), Marker M16 (SEQ ID NO: 16), and Marker M17 (SEQ ID NO: 17) in said plant. In further embodiments, the chromosomal segment comprises a marker locus selected from the group consisting of Marker M18 (SEQ ID NO: 18), Marker M19 (SEQ ID NO: 19), Marker M20 (SEQ ID NO: 20), Marker M21 (SEQ ID NO: 21), Marker M22 (SEQ ID NO: 22), Marker M23 (SEQ ID NO: 23), Marker M24 (SEQ ID NO: 24), Marker M25 (SEQ ID NO: 25), Marker M26 (SEQ ID NO: 26), Marker M27 (SEQ ID NO: 27), and Marker M28 (SEQ ID NO: 28) on chromosome 6. In some embodiments, the chromosomal segment is located between 26,405 bp and 213,924,156 bp on chromosome 6 of public pepper genome sequence Pepper CM334 v.1.55. In some embodiments, the chromosomal segment comprises the haplotype of variety Ganti, wherein a representative sample of seed of said variety has been deposited under NCIMB accession number 43055. In other embodiments, the chromosomal segment comprises the haplotype of variety Flame Fountain, wherein a representative sample of seed of said variety has been deposited under NCIMB accession number 43054.

The present invention also provides a seed that produces a *Capsicum annuum* plant comprising a *Capsicum baccatum* cytoplasm and comprising a chromosomal segment on chromosome 6 that confers male fertility in a male sterile *Capsicum annuum* plant comprising a *Capsicum baccatum* cytoplasm relative to a plant lacking said chromosomal segment.

Additionally, the present invention provides a plant part of a *Capsicum annuum* plant comprising a *Capsicum baccatum* cytoplasm and comprising a chromosomal segment on chromosome 6 that confers male fertility in a male sterile *Capsicum annuum* plant comprising a *Capsicum baccatum* cytoplasm relative to a plant lacking said chromosomal segment. In certain embodiments, the plant part is a cell, a seed, a root, a stem, a leaf, a flower, a fruit, or pollen.

The present invention also provides a *Capsicum annuum* plant comprising a *Capsicum baccatum* cytoplasm and comprising a chromosomal segment on chromosome 6 that confers male fertility in a male sterile *Capsicum annuum* plant comprising a *Capsicum baccatum* cytoplasm relative to a plant lacking said chromosomal segment, wherein the plant is a sweet pepper variety.

Additionally, the present invention provides a *Capsicum annuum* plant comprising a *Capsicum baccatum* cytoplasm and comprising a chromosomal segment on chromosome 6 that confers male fertility in a male sterile *Capsicum annuum* plant comprising a *Capsicum baccatum* cytoplasm relative to a plant lacking said chromosomal segment, wherein the plant has a blocky type fruit shape.

The present invention also provides a *Capsicum annuum* plant comprising a *Capsicum baccatum* cytoplasm and comprising a chromosomal segment on chromosome 6 that confers male fertility in a male sterile *Capsicum annuum* plant comprising a *Capsicum baccatum* cytoplasm relative to a plant lacking said chromosomal segment, wherein said plant further comprises a chromosomal segment from *Capsicum baccatum* on chromosome 6 that confers uniform female fertility in a male sterile *Capsicum annuum* plant comprising a *Capsicum baccatum* cytoplasm relative to a plant lacking said chromosomal segment, wherein said chromosomal segment from *Capsicum baccatum* is flanked by Marker A12 (SEQ ID NO: 35) and Marker A35 (SEQ ID NO: 36) in said plant.

In another aspect, the present invention provides a method for producing a *Capsicum annuum* plant that confers male fertility in a male sterile *Capsicum annuum* plant comprising a *Capsicum baccatum* cytoplasm, comprising introgressing into said plant a chromosomal segment on chromosome 6 that confers male fertility in a male sterile *Capsicum annuum* plant comprising a *Capsicum baccatum* cytoplasm relative to a plant lacking said chromosomal segment. In some embodiments, the introgressing comprises crossing a plant comprising said chromosomal segment with itself or with a second *Capsicum annuum* plant of a different genotype to produce one or more progeny plants, and selecting a progeny plant comprising said chromosomal segment. In further embodiments, the selecting a progeny plant comprises detecting at least one allele flanked by Marker M29 (SEQ ID NO: 29) and a marker selected from the group consisting of Marker M14 (SEQ ID NO: 14), Marker M15 (SEQ ID NO: 15), Marker M16 (SEQ ID NO: 16), and Marker M17 (SEQ ID NO: 17) on chromosome 6. In other embodiments, the progeny plant is an $F_2$-$F_6$ progeny plant. In particular embodiments, the crossing comprises backcrossing, which in certain embodiments comprises from 2-7 generations of backcrosses.

The present invention also provides a *Capsicum annuum* plant produced by a method comprising introgressing into said plant a chromosomal segment on chromosome 6 that confers male fertility in a male sterile *Capsicum annuum* plant comprising a *Capsicum baccatum* cytoplasm relative to a plant lacking said chromosomal segment. Thus, the present invention also provides a method of producing food or feed comprising obtaining a *Capsicum annuum* plant comprising a *Capsicum baccatum* cytoplasm and comprising a chromosomal segment on chromosome 6 that confers male fertility in a male sterile *Capsicum annuum* plant comprising a *Capsicum baccatum* cytoplasm relative to a plant lacking said chromosomal segment, or a part thereof, and producing said food or feed from said plant or part thereof.

In another aspect, the present invention provides a *Capsicum annuum* plant obtainable by a method comprising the step of introgressing into a plant a male fertility restoration locus allele for *Baccatum* cytoplasmic male sterility, wherein said male fertility restoration locus allele is defined as located in a chromosomal segment flanked by Marker M29 (SEQ ID NO: 29) and a marker selected from the group consisting of Marker M14 (SEQ ID NO: 14), Marker M15 (SEQ ID NO: 15), Marker M16 (SEQ ID NO: 16), and Marker M17 (SEQ ID NO: 17) on chromosome 6. In certain embodiments, the introgressing comprises backcrossing. In other embodiments, the introgressing comprises marker-assisted selection.

BRIEF DESCRIPTION OF THE DRAWINGS

FIG. 1: Shows an overview of the genetic model for the functioning of the *Baccatum* cytoplasmic male sterility (CMS) system. The phenotypic predictions are for plants with *Capsicum baccatum* cytoplasm.

FIG. 3: Shows a schematic of the genetic model for Gf and Rf transmission in pepper plants having a *Capsicum baccatum* or a *Capsicum annuum* cytoplasm. The "(S)" denotes a *Capsicum baccatum* cytoplasm and the "(N)" denotes a *Capsicum annuum* cytoplasm. Fn progeny derived from restored F1 plants (e.g. BCMS Donor Line 1×'Flame Fountain') segregate for 50% completely fertile and 50% male sterile plants.

DETAILED DESCRIPTION

Figure 2:
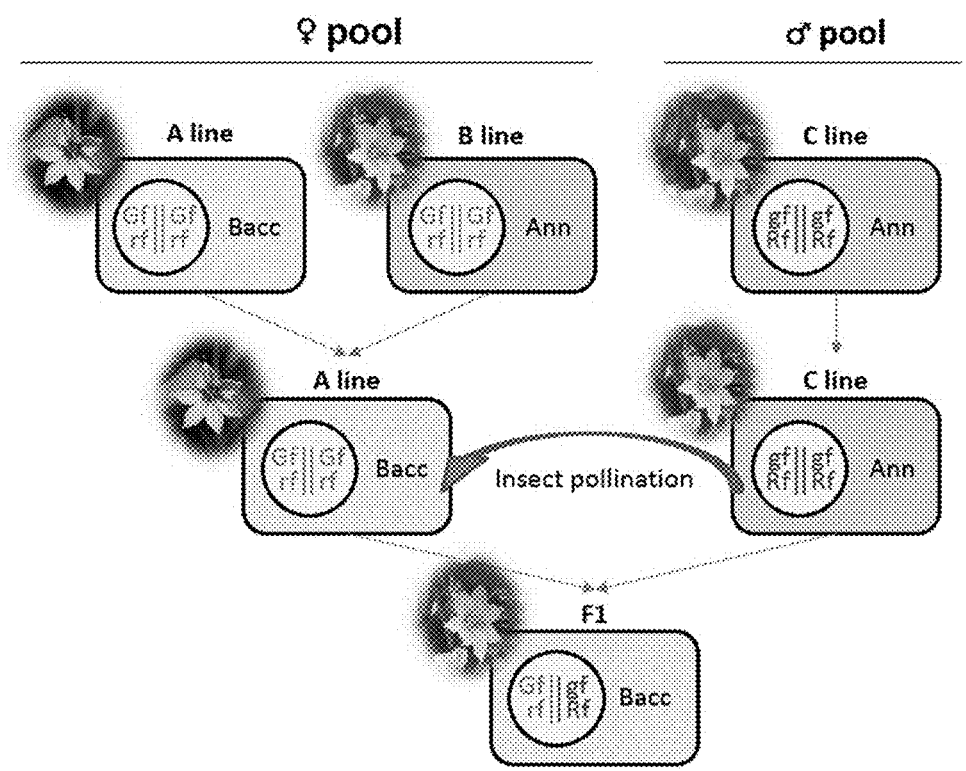
FIG. 2: Shows a schematic of the hybrid production concept with CMS, based on *Capsicum baccatum* cytoplasm. The female pool comprises two lines that lack the male fertility restorer locus: the A-line, which is a male sterile line that serves as the female parent in the hybrid cross; and the B-line, which is a male fertile line that serves as the maintainer and enables crosses within the female breeding pool. The C-line serves as the male parent of the hybrid cross and generally is a normal *Capsicum annuum* line that lacks the Gf locus, but is fixed for the male fertility restorer locus allele Rf. "Bacc" indicates plants with a *Capsicum baccatum* cytoplasm, while "Ann" indicates plants with a *Capsicum annuum* cytoplasm.

Male sterility is used by breeders for two basic product concepts in a variety of crops. The first product concept is seedless fruit. Plants comprising the male sterility trait are crossed with plants comprising parthenocarpy genes to produce hybrid seed. This hybrid seed produces plants bearing seedless fruit. Under normal circumstances, male sterile plants cannot set fruit in the absence of pollination. However, if the plant also contains parthenocarpy genes, then fruit set occurs in the absence of pollination. In this product concept, it is possible to use different forms of male sterility without a restorer locus. However, only cytoplasmic male sterility will allow for production of seed from which 100% of the plants grown from this seed are sterile and bear seedless fruit. Using genic male sterility for this product concept requires an intermediate seedling selection step after showing the hybrid seed, followed by transplanting or grafting of the selected sterile plants. The second product concept is one where male sterility is used to easily develop hybrid seed. In the development of hybrid seed it is important to ensure genetic purity of a seed batch. This entails minimizing the number of seed that are the result of self-fertilization. Self-fertilization is prevented during seed production through physical removal of male sex organs in the flower before the flower opens, a process referred to as emasculation. This is a labor-intensive procedure that is not only costly, but also is not 100% effective. Genetic emasculation of the female line overcomes these limitations and ensures the genetic purity of the hybrid seed. However, successful hybrid production requires that the male sterility system used can be restored in the hybrid. Thus, the male parent of the hybrid will typically contain a dominant male fertility restorer locus. When a male parent comprising the restorer locus is crossed with the male sterile female parent, fully fertile hybrid plants will be produced. Given that resultant hybrid plants are heterozygous, it is essential that the restorer locus be dominant.

Genetic (or genic) male sterility (GMS) systems utilize male sterility loci that are often inherited in a recessive manner and encoded within the nuclear genome. An exception to this is, for example, a GMS system in rapeseed where both the sterility and sterility suppressor genes are dominant. A primary disadvantage with the genetic male sterility system is that only half of the progeny plants will be male sterile. A breeder would therefore have to select which plants are suitable for hybrid/seedless fruit production post-germination, resulting in at least half of the seedlings being discarded. A system that does not have this problem is the cytoplasmic male sterility (CMS) system. In this system, the male sterility loci are coded in the mitochondrial DNA and, in the absence of a nuclear male fertility restoration gene, 100% of the progeny plants are male sterile. In pepper, the Peterson's CMS system is widely used because a dominant male fertility restoration locus is available, making this system suitable for both hybrid production and the seedless fruit concept. The restorer locus for Peterson's CMS is often referred to as the CMS restorer locus or Rf. The CMS restorer allele (Rf) was identified in pungent *Capsicum annuum* germplasm and has been mapped to a locus on the short arm of chromosome 6. Transferring a functioning restorer locus to sweet pepper types has proven difficult and remains the subject of much study and breeding efforts because the Peterson's CMS system is known to be unstable with respect to environmental conditions and genetic background.

An environmentally-stable alternative to the Peterson's CMS system is the *Baccatum* cytoplasmic male sterility (BCMS) system. This system was created by crossing a female *Capsicum baccatum* plant with a male *Capsicum annuum* plant. The resulting hybrid, which was obtained through a step of embryo rescue, contained a *Capsicum baccatum* cytoplasm and was male sterile. Through extensive backcrossing to the *Capsicum annuum* parent, the *Capsicum baccatum* genome was replaced with *Capsicum annuum* DNA. However, the BCMS system has some limitations. First, female sterility segregates within the population of BCMS lines and efforts to eliminate this negative trait through crossing and selection has not been successful. Second, there does not appear to be a dominant restorer locus for the BCMS, in the absence of a nuclear male fertility restoration gene.

The present inventors have found that the limitation of use of the BCMS system due to the lack of a dominant restorer locus can be overcome by use of a chromosomal segment from certain *Capsicum annuum* lines on the short arm of chromosome 6 that confers male fertility in BCMS pepper lines. This locus was identified in the varieties 'Ganti' (NCIMB 43055) and 'Flame Fountain' (NCIMB 43054) in a study of BCMS male fertility restoration using *Capsicum annuum* accessions. The variety 'Ganti' is a landrace from Hungary that is best described as a sweet Hungarian-white or Hungarian-wax type pepper. The variety 'Flame Fountain' is a hot Indian-type pepper that is characterized by a long and thin fruit that colors green to red. Surprisingly, although the novel male fertility restoration locus of the invention is located on the same chromosome as the CMS restorer allele used in the Peterson's CMS system, it was found that they are distinct, as crosses between BCMS plants and plants with the Peterson's CMS fertility restorer locus did not result in male fertility restoration. The invention therefore provides methods and compositions for restoring male fertility in BCMS pepper plants, as well as markers for tracking and identifying the novel chromosomal segment in plants during breeding. A non-limiting summary of useful markers is provided in Table 1. The chromosomal segment is located between markers M1 (SEQ ID NO: 1) and M34 (SEQ ID NO: 34), while markers M2 to M33 can also be used to select the chromosomal segment in subsequent germplasm. The specific selected markers used depends on the polymorphism between the male fertility locus donor ('Ganti' or 'Flame Fountain') and the non-donor parent (recurrent parent). Therefore, a combination of markers listed in Table 1 may be used for benefit in a first selection, while markers can be limited to a polymorphic subset in a given cross for further selections.

I. GENOMIC REGIONS, ALLELES, AND POLYMORPHISMS ASSOCIATED WITH MALE FERTILITY IN BCMS LINES

The inventors identified a novel chromosomal segment on chromosome 6 from *Capsicum annuum* that confers male fertility in a *Baccatum* cytoplasmic male sterile plant, together with polymorphic nucleic acids and linked markers for tracking and introgressing the chromosomal segment into potentially any variety during plant breeding. The newly identified chromosomal segment on chromosome 6 from donor line 'Ganti' covers a region of 31.7 cM and is flanked by marker M1, a SNP change [A/G] at 213,924,156 bp on genome sequence version 1.55 of pepper line CM334, which can be found at solgenomics.net, and marker M34, a SNP change [G/C] at 21,133,217 bp. Interstitial markers, such as M2, a SNP change [C/T] at 213,907,080 bp, M3, a SNP change [A/G] at 213,907,920 bp, M4, a SNP change [T/C] at 427,239 bp, M6, a SNP change [T/C] at 87,022 bp, M8, a SNP change [C/T] at 89,795 bp, M12, a SNP change [A/C] at 3,009,771 bp, M13, a SNP change [C/T] at 2,999,718 bp, M14, a SNP change [G/T] at 3,504,248 bp, M18, a SNP change [A/G] at 3,475,770 bp, M19, a SNP change [G/T] at 3,422,765 bp, M20, a SNP change [A/T] at 4,276,008 bp, M23, a SNP change [A/G] at 70,994,266 bp, M27, a SNP change [T/G] at 8,522,176 bp, M28, a SNP change [A/G] at 9,799,932 bp, and M33, a SNP change [C/T] at 11,592,142 bp, can be used in any possible combination as flanking markers to select for the restorer locus on chromosome 6 from Ganti or another donor line.

The newly identified chromosomal segment on chromosome 6 from donor line 'Flame Fountain' covers a region of 24.9 cM and is flanked by marker M5, a SNP change [A/G] at 428,143 bp on genome sequence version 1.55 of pepper line CM334, which can be found at solgenomics.net, and marker M33, a SNP change [C/T] at 11,592,142 bp. Interstitial markers, such as M7, a SNP change [C/T] at 125,861 bp, M8, a SNP change [C/T] at 89,795 bp, M11, a SNP change [A/G] at 3,055,268 bp, M12, a SNP change [A/C] at 3,009,771 bp, M13, a SNP change [C/T] at 2,999,718 bp, M14, a SNP change [G/T] at 3,504,248 bp, M15, a SNP change [C/A] at 3,500,133 bp, M16, a SNP change [A/G] at 3,505,583 bp, M17, a SNP change [C/T] at 3,308,938 bp, M18, a SNP change [A/G] at 3,475,770 bp, M19, a SNP change [G/T] at 3,422,765 bp, M20, a SNP change [A/T] at 4,276,008 bp, M25, a SNP change [G/A] at 6,240,565 bp, and M26, a SNP change [C/T] at 6,241,544 bp, can be used in addition to the flanking markers to select for the restorer locus on chromosome 6 from Flame Fountain or another donor line.

Additionally, interstitial markers, such as M5, a SNP change [A/G] at 428,143 bp, M7, a SNP change [C/T] at 125,861 bp, M9, a SNP change [T/C] at 386,489 bp, M10, a SNP change [C/A] at 26,405 bp, M21, a SNP change [G/A] at 4,240,789 bp, M22, a SNP change [G/C] at 4,245,699 bp, M24, a SNP change [A/T] at 4,240,551 bp, M29, a SNP change [C/T] at 10,670,362 bp, M30, a SNP change [T/C] at 10,664,163 bp, M31, a SNP change [G/T] at 10,664,630 bp, and M32, a SNP change [T/C] at 11,108,817 bp, can be used in addition to the flanking markers to select for the restorer locus on chromosome 6 from either donor line 'Ganti' or 'Flame Fountain' or another donor line. Thus, the present disclosure provides a *Capsicum annuum* plant comprising a chromosomal segment on chromosome 6 of *Capsicum annuum* flanked by markers M1 and M34 that confers male fertility to BCMS pepper plants. In certain embodiments, one or both of the flanking markers are interstitial markers between M1 and M34, such as markers M2, M3, M4, M5, M6, M7, M8, M9, M10, M11, M12, M13, M14, M15, M16, M17, M18, M19, M20, M21, M22, M23, M24, M25, M26, M27, M28, M29, M30, M31, M32, or M33 and comprise an allele from 'Ganti' or 'Flame Fountain' at said marker(s). In some embodiments, the chromosomal segment on chromosome 6 of *Capsicum annuum* comprises a plurality of the markers listed in Table 1, including any possible combination thereof. In some embodiments, the chromosomal segment on chromosome 6 of *Capsicum annuum* restoring fertility in plants with *Capsicum baccatum* cytoplasmic male sterility from 'Ganti' is flanked by markers M14 and M29, wherein interstitial markers M15, M16, M17, M18, M19, M20, M21, M22, M23, M24, M25, M26, M27, M28 or any combination thereof are used to select this region. In some embodiments, the chromosomal segment on chromosome 6 of *Capsicum annuum* restoring fertility in plants with *Capsicum baccatum* cytoplasmic male sterility from 'Flame Fountain' is flanked by markers M17 and M29, wherein interstitial markers M18, M19, M20, M21, M22, M23, M24, M25, M26, M27, M28 or any combination thereof are used to select this region.

II. INTROGRESSION OF GENOMIC REGIONS ASSOCIATED WITH RESTORATION OF MALE FERTILITY

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The invention provides a *Capsicum annuum* plant comprising an introgressed allele on chromosome 6 that confers male fertility in a pepper plant with BCMS, wherein said allele is located between marker M2 and marker M33, or preferably between marker M14 and marker M29. In addition, the invention provides a *Capsicum annuum* plant with a cytoplasm from *Capsicum baccatum*, in which male fertility is restored due to the presence of a male fertility restoration allele on chromosome 6, wherein said allele is located between marker M2 and marker M33, or preferably between marker M14 and marker M29. In some embodiments, the plant is a variety selected from the group consisting of Anaheim, Ancho/Poblano, Asian Long Slim, Asian Short, Blocky or Bell, Capia, Cascabel, Cayenne, Chiltepins or Small Hots, Corno di Toro, Cubanelle, 'Fresno Chili', Hungarian Wax/Banana/Hungarian White, Jalapeno, Ornamental, Pasilla, Pimiento, Santa Fe Grande, Serrano, and Waxy peppers. In certain embodiments, the plant has a blocky type fruit shape, a ¾ long type fruit shape, or a half long type fruit shape. For example, the fruit of the plant may have a length to width ratio less than 2.5:1, such as a length to width ratio of less than 2:1, or a length to width ratio of between 0.8 to 1.2. As used herein, blocky type pepper refers to a pepper wherein the length of the fruit is about the same as the width of the fruit. For example, the length of the fruit is about 0.8, about 0.9, about 1.0, about 1.1, or less than 1.2 of the width of the fruit. As used herein, ¾ long type pepper, often known as lamuyo, refers to a pepper wherein the length of the fruit is more than about 1.5 of the width of the fruit. These peppers can have a variety of different colors, for example white, purple, and green at the immature stage, and for example red, yellow, green, orange, and brown at the mature fruit stage. It is also well-known that definitions vary regionally. For example, in the United States peppers with a length to with ratio of 1.2 to 1.4 are often referred to as "deep blocky", while the terms half long and lamuyo are used interchangeably for sweet peppers with a length to width ratio over 1.4.

In certain embodiments, the genomic regions identified herein may be introgressed from any *Capsicum annuum* type into any *Capsicum annuum* type. Types of *Capsicum annuum* include, but are not limited to Anaheim, Ancho/Poblano, Asian long slim, Asian short, Blocky or Bell, Capia, Cascabel, Cayenne, Chiltepins or Small Hots, Corno di Toro, Cubanelle, 'Fresno Chili', Jalapeno, Ornamental, Pasilla, Pimiento, Santa Fe Grande, Serrano, and Waxy peppers, including Hungarian wax/Banana/Hungarian white.

In certain embodiments, the identified genomic regions are introduced into a jalapeno variety. Pepper fruit shapes are well-known to those skilled in the art of pepper breeding. Jalapeno peppers are a type of *Capsicum annuum* that have a characteristic fruit shape. Jalapeno fruits are typically bullet-shaped and have a length to width ratio of about 2.5 to 1. For example, a fruit having a length of about 10 cm would be expected to be about 4 cm wide. The fruit typically has thick walls of about 5-6 mm and the dry matter content is normally around 7%. The fruit of most plants develops from a medium green at the immature stage to red at the mature stage. As a commercial product, the fruits are harvested at the green stage. The pungency of jalapeno peppers varies from 0 units to over 5000 units on the Scoville scale.

The present invention provides novel markers for identifying and tracking introgression of one or more of the genomic regions from a donor plant comprising male fertility restoration alleles into *Baccatum* cytoplasmic male sterility lines. The invention further provides markers for identifying and tracking the novel introgressions disclosed herein during plant breeding, including the markers set forth in Table 1.

Markers within or linked to any of the genomic intervals of the present invention can be used in a variety of breeding efforts that include introgression of genomic regions associated with male fertility into a desired genetic background. For example, a marker within 30 cM, 25 cM, 20 cM, 16 cM, 15 cM, 10 cM, 5 cM, 2 cM, or 1 cM of a marker associated with male fertility described herein can be used for marker-assisted introgression of genomic regions associated with a male fertility phenotype.

Pepper plants comprising one or more introgressed regions associated with a desired phenotype wherein at least 10%, 25%, 50%, 75%, 90%, or 99% of the remaining genomic sequences carry markers characteristic of the germplasm are also provided. Pepper plants comprising an introgressed region comprising regions closely linked to or adjacent to the genomic regions and markers provided herein and associated with a male fertility phenotype are also provided.

III. DEVELOPMENT OF PEPPER PLANTS THAT PROVIDE MALE FERTILITY

For most breeding objectives, commercial breeders work within germplasm that is "cultivated type" or "elite." This germplasm is easier to breed because it generally performs well when evaluated for horticultural performance. For example, *Capsicum annuum* is an agronomically elite, cultivated pepper adapted to commercial use. However, the performance advantage a cultivated germplasm provides can be offset by a lack of allelic diversity. Breeders generally accept this tradeoff because progress is faster when working with cultivated material than when breeding with genetically diverse sources.

In contrast, when a breeder makes either intraspecific crosses, or interspecific crosses, a converse tradeoff occurs. In these examples, a breeder typically crosses germplasm of an economically important species with a non-cultivated or commercially unacceptable species. The breeder can gain access to novel alleles from the non-cultivated species, but may have to overcome genetic drag or interspecific hybridization barriers associated with such crosses. Because of the difficulty with this breeding strategy, this approach often fails because of fertility and fecundity problems. The difficulty with this breeding approach extends to many crops, and is exemplified with an important disease resistant phenotype that was first described in tomato in 1944 (Smith, *Proc. Am. Soc. Hort. Sci.* 44:413-16). In this cross, a nematode disease resistance was transferred from *L. peruvianum* (PI128657) into a cultivated tomato. Despite intensive breeding, it was not until the mid-1970's before breeders could overcome the genetic drag and release successful lines carrying this trait. Indeed, even today, tomato breeders deliver this disease resistance gene to a hybrid variety from only one parent. This allows the remaining genetic drag to be masked. The inventiveness of succeeding in this breeding approach has been recognized by the USPTO (U.S. Pat. Nos. 6,414,226, 6,096,944, 5,866,764, and 6,639,132).

The process of introgressing desirable genes from one species into another while avoiding problems with linkage drag or low heritability is a long and often arduous process. Success in deploying alleles derived from related species therefore strongly depends on minimal or truncated introgressions that lack detrimental effects and reliable marker assays that replace phenotypic screens. Success is further defined by simplifying genetics for key attributes to allow focus on genetic gain for quantitative traits. Moreover, the process of introgressing genomic regions from non-cultivated lines or different species can be greatly facilitated by the availability of informative markers.

One of skill in the art would therefore understand that the alleles, polymorphisms, and markers provided by the invention allow the tracking and introduction of any of the genomic regions identified herein into any genetic background. In addition, the genomic regions associated with male fertility disclosed herein can be introgressed from one genotype to another and tracked phenotypically or genetically. Thus, Applicants' discovery of accurate markers associated with male fertility restoration locus will facilitate the development of pepper plants having beneficial phenotypes. For example, plants and seeds can be genotyped using the markers of the present invention in order to develop varieties comprising desired male fertility. Moreover, marker-assisted selection (MAS) allows identification of plants which are homozygous or heterozygous for the desired introgression.

Meiotic recombination is essential for plant breeding because it enables the transfer of favorable alleles across genetic backgrounds, the removal of deleterious genomic fragments, and pyramiding traits that are genetically tightly linked. In the absence of accurate markers, limited recombination forces breeders to enlarge segregating populations for progeny screens. Moreover, phenotypic evaluation is time-consuming, resource-intensive and not reproducible in every environment. The markers provided by the invention offer an effective alternative and therefore represent a significant advance in the art.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among pepper species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

Many desirable traits that are successfully introduced through introgression can also be introduced directly into a plant by the use of molecular techniques. One aspect of the invention includes plants with a genome that has been changed by any method using site-specific genome modification techniques. Techniques of site-specific genome modification include the use of enzymes such as, endonucleases, recombinases, transposases, helicases and any combination thereof. In one aspect, an endonuclease is selected from a meganuclease, a zinc-finger nuclease (ZFN), a transcription activator-like effector nucleases (TALEN), an Argonaute, and an RNA-guided nuclease, such as a CRISPR associated nuclease.

In another aspect, the endonuclease is a dCas9-recombinase fusion protein. As used herein, a "dCas9" refers to a Cas9 endonuclease protein with one or more amino acid mutations that result in a Cas9 protein without endonuclease activity, but retaining RNA-guided site-specific DNA binding. As used herein, a "dCas9-recombinase fusion protein" is a dCas9 with a protein fused to the dCas9 in such a manner that the recombinase is catalytically active on the DNA.

Non-limiting examples of recombinase include a tyrosine recombinase attached to a DNA recognition motif provided herein is selected from the group consisting of a Cre recombinase, a Gin recombinase a Flp recombinase, and a Tnp1 recombinase. In an aspect, a Cre recombinase or a Gin recombinase provided herein is tethered to a zinc-finger DNA-binding domain, or a TALE DNA-binding domain, or a Cas9 nuclease. In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

Site-specific genome modification enzymes, induce a genome modification such as a double-stranded DNA break (DSB) or single-strand DNA break at the target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of exogenous sequences by homologous recombination.

Another aspect of the invention includes transgenic plant cells, transgenic plant tissues, transgenic plants, and transgenic seeds that comprise the recombinant DNA molecules and engineered proteins provided by the invention. These cells, tissues, plants, and seeds comprising the recombinant DNA molecules and engineered proteins exhibit resistance to *P. capsici*. Suitable methods for transformation of host plant cells for use with the current invention include virtually any method by which DNA can be introduced into a cell (for example, where a recombinant DNA construct is stably integrated into a plant chromosome) and are well known in the art. An exemplary and widely utilized method for introducing a recombinant DNA construct into plants is the *Agrobacterium* transformation system, which is well known to those of skill in the art. Another exemplary method for introducing a recombinant DNA construct into plants is insertion of a recombinant DNA construct into a plant genome at a pre-determined site by methods of site-directed integration. Transgenic plants can be regenerated from a transformed plant cell by the methods of plant cell culture. A transgenic plant homozygous with respect to a transgene (that is, two allelic copies of the transgene) can be obtained by self-pollinating (selfing) a transgenic plant that contains a single transgene allele with itself, for example an R0 plant, to produce R1 seed. One fourth of the R1 seed produced will be homozygous with respect to the transgene. Plants grown from germinating R1 seed can be tested for zygosity, using a SNP assay, DNA sequencing, or a thermal amplification assay that allows for the distinction between heterozygotes and homozygotes, referred to as a zygosity assay.

IV. MOLECULAR ASSISTED BREEDING TECHNIQUES

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Vegetable breeders use molecular markers to interrogate a crop's genome and classify material based on genetic, rather than phenotypic, differences. Advanced marker technologies are based on genome sequences, the nucleotide order of distinct, polymorphic genotypes within a species. Such platforms enable selection for horticultural traits with markers linked to favorable alleles, in addition to the organization of germplasm using markers randomly distributed throughout the genome. In the past, a priori knowledge of the genome lacked for major vegetable crops that now have been sequenced. Scientists exploited sequence homology, rather than known polymorphisms, to develop marker platforms. Man-made DNA molecules are used to prime replication of genome fragments when hybridized pair-wise in the presence of a DNA polymerase enzyme. This synthesis, regulated by thermal cycling conditions that control hybridization and replication of DNA strands in the polymerase chain reaction (PCR) to amplify DNA fragments of a length dependent on the distance between each primer pair. These fragments are then detected as markers and commonly known examples include AFLP and RAPD. A third technique, RFLP does not include a DNA amplification step. Amplified fragment length polymorphism (AFLP) technology reduces the complexity of the genome. First, through digestive enzymes cleaving DNA strands in a sequence-specific manner. Fragments are then selected for their size and finally replicated using selective oligonucleotides, each homologous to a subset of genome fragments. As a result, AFLP technology consistently amplifies DNA fragments across genotypes, experiments and laboratories.

Polymorphisms comprising as little as a single nucleotide change can be assayed in a number of ways. For example, detection can be made by electrophoretic techniques including a single strand conformational polymorphism, denaturing gradient gel electrophoresis, or cleavage fragment length polymorphisms, but the widespread availability of DNA sequencing often makes it easier to simply sequence amplified products directly. Once the polymorphic sequence difference is known, rapid assays can be designed for progeny testing, typically involving some version of PCR amplification of specific alleles or PCR amplification of multiple specific alleles.

Polymorphic markers serve as useful tools for assaying plants for determining the degree of identity of lines or varieties. These markers form the basis for determining associations with phenotypes and can be used to drive genetic gain. In certain embodiments of methods of the invention, polymorphic nucleic acids can be used to detect in a *Capsicum annuum* plant a genotype associated with male fertility, identify a *Capsicum annuum* plant with a genotype associated with male fertility, and to select a *Capsicum annuum* plant with a genotype associated with male fertility. In certain embodiments of methods of the invention, polymorphic nucleic acids can be used to produce a *Capsicum annuum* plant that comprises in its genome an introgressed locus associated with male fertility. In certain embodiments of the invention, polymorphic nucleic acids can be used to breed progeny *Capsicum annuum* plants comprising a locus associated with male fertility.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e., for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with male fertility in BCMS plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) using primer pairs that are capable of hybridizing to the proximal sequences that define a polymorphism in its double-stranded form. Methods for typing DNA based on mass spectrometry can also be used. Such methods are well known in the art.

Polymorphisms in DNA sequences can be detected or typed by a variety of effective methods well known in the art. The compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe. Target nucleic acid sequence can also be detected by probe ligation methods where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization. On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms.

Other well-known methods for detecting SNPs and Indels include single base extension (SBE) methods. In another method for detecting polymorphisms, SNPs and Indels can be detected by methods in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5' 4 3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

V. DEFINITIONS

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which *Capsicum annuum* plants can be regenerated, plant calli, plant clumps and plant cells that are intact in plants or parts of plants such as pollen, flowers, seeds, leaves, stems, and the like.

As used herein, "blocky" type pepper refers to a pepper wherein the length of the fruit is about the same as the width of the fruit. For example, the length of the fruit is about 0.8, about 0.9, about 1.0, about 1.1, or less than 1.2 of the width of the fruit.

As used herein, "sweet" pepper refers to the fruit and the plant of the non-pungent chili pepper varieties. Sweet peppers belong to the genus *Capsicum*, of the nightshade family, Solanaceae. The term "sweet pepper" therefore includes bell peppers (*Capsicum annuum*), the "Thai sweet"—also a cultivar of *Capsicum annuum*, the "dulce"—a popular cultivar of *Capsicum baccatum*, as well as Numex Suave Orange (*Capsicum chinense*), an unusually sweet habanero-type pepper.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, the term "haplotype" means a chromosomal segment defined by the combination of alleles it carries.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, marker assisted selection, various plant transformation techniques and/or methods that provide for homologous recombination, non-homologous recombination, site-specific recombination, and/or genomic modifications that provide for locus substitution or locus conversion.

As used herein, the term "linked," when used in the context of nucleic acid markers and/or genomic regions, means that the markers and/or genomic regions are located on the same linkage group or chromosome such that they tend to segregate together at meiosis.

As used herein, "cytoplasmic male sterility" refers to plants that are not usually capable of breeding from self-pollination due to the failure of the plant to produce functional anthers, pollen, or male gametes in absence of a male fertility restorer locus, but are capable of breeding from being cross-pollinated when used as the female parent. Furthermore, the male sterility is the result of an incompatibility between the cytoplasm and the nuclear genome.

As used herein, "*Baccatum* cytoplasmic male sterility" or "BCMS" refers to cytoplasmic male sterile plants wherein the cytoplasm is from a *Capsicum baccatum* plant and the nuclear genome from a *Capsicum annuum* plant.

As used herein, a "female parent" refers to a pepper plant that is the recipient of pollen from a male donor line, which pollen successfully pollinates an egg. A female parent can be any pepper plant that is the recipient of pollen. Such female parents can be male sterile, for example, because of genic male sterility, cytoplasmic male sterility, or because they have been subject to physical emasculation of the stamens. Genic or cytoplasmic male sterility can be manifested in different manners, such as sterile pollen, malformed or stamenless flowers, positional sterility, and functional sterility.

As used herein, "uniform female fertility" refers to the production of male sterile flowers that are otherwise developmentally normal (i.e. female fertile) and produce viable fruit and seed if fertilized with a male fertile pollen source. A locus that confers uniform female fertility means that all flowers of a *Baccatum* cytoplasmic male sterile plant carrying the locus will comprise functioning female organs and non-functioning male organs, in absence of a male fertility restoration locus.

As used herein, "good flower" refers to pepper plants comprising a flower that is female fertile and developmentally normal. Plants with good flowers can be male fertile or male sterile.

As used herein, "male parent plant" refers to a parent plant that provides pollen to (i.e. is a pollinator for) a female line. They may be useful for breeding of progeny pepper plants, such as parthenocarpic seedless progeny plants.

As used herein, "resistance allele" means the nucleic acid sequence associated with resistance or tolerance to disease.

As used herein "resistance" or "improved resistance" in a plant to disease conditions is an indication that the plant is less affected by disease conditions with respect to yield, survivability and/or other relevant agronomic measures, compared to a less resistant, more "susceptible" plant. Resistance is a relative term, indicating that a "resistant" plant survives and/or produces better yields in disease conditions compared to a different (less resistant) plant grown in similar disease conditions. As used in the art, disease "tolerance" is sometimes used interchangeably with disease "resistance." One of skill will appreciate that plant resistance to disease conditions varies widely, and can represent a spectrum of more-resistant or less-resistant phenotypes. However, by simple observation, one of skill can generally determine the relative resistance or susceptibility of different plants, plant lines or plant families under disease conditions, and furthermore, will also recognize the phenotypic gradations of "resistant."

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

VI. DEPOSIT INFORMATION

Deposits of seeds of *Capsicum annuum* lines designated 'Flame Fountain' and 'Ganti,' which are disclosed herein above and referenced in the claims, were made with NCIMB, Ferguson Building, Craibstone Estate, Bucksburn, Aberdeen, AB21 9YA, Scotland, U.K. The date of deposit was May 29, 2018 and the accession numbers for those deposited seeds of lines 'Flame Fountain' and 'Ganti' are NCIMB Accession Nos. 43054 and 43055, respectively. All restrictions upon the deposits have been removed, and the deposits are intended to meet all of the requirements of 37 C.F.R. § 1.801-1.809. The deposits have been accepted under the Budapest Treaty and will be maintained in the depository for a period of 30 years, or 5 years after the last request, or for the effective life of the patent, whichever is longer, and will be replaced if necessary during that period.

VII. EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1. Creation of a BCMS *Capsicum annuum* Plant

The compatibility between *Capsicum annuum* and *Capsicum baccatum* for interspecific crosses is very low. To transfer genetic information between these two species, intermediate pepper species, such as *Capsicum chinense* or *Capsicum frutescens*, have been used as a 'genetic bridge'. However, this method only allows for the transfer of nuclear traits. To develop a BCMS plant where a *Capsicum annuum* genome is introduced into a *Capsicum baccatum* cytoplasm, it is necessary to pollenate a *Capsicum baccatum* flower with *Capsicum annuum* pollen. These combinations never led to viable hybrid seed and it was therefore necessary to use embryo rescue techniques to recover a *Capsicum baccatum*×*Capsicum annuum* hybrid. The method described herein was used to develop *Capsicum baccatum*×*Capsicum annuum* hybrids from several *Capsicum baccatum* accessions, such as PI497974, PI159242, and PI640880.

Plants of these *Capsicum baccatum* accessions were grown simultaneously with *Capsicum annuum* lines that served as pollen donors. Flowers on the *Capsicum baccatum* plants were emasculated before the anthers shed and subsequently pollinated with the *Capsicum annuum* pollen. One day after the first pollination, the pollinated flowers were dipped in 200 mg/L NAA (1-naphthylacetic acid) followed by a second pollination after the NAA solution (growth regulator) had dried. The flowers were then left to develop fruit. Ripe fruit were harvested and seeds were extracted from the fruit for embryo rescue. The embryo rescue was performed under aseptic conditions by dissecting the embryos from endosperms. The extracted embryos were cultured on MS media until seedlings had fully developed. These $F_1$ seedlings were checked for *Capsicum baccatum*× *Capsicum annuum* hybridization using polymorphic DNA markers. Seedlings that were true hybrids were selected for further backcrossing to the *Capsicum annuum* parent. Early backcross generations were selected phenotypically for male sterility and the *Capsicum annuum* recurrent parent phenotype and the genome was evaluated for *Capsicum annuum* percentage using polymorphic DNA markers. In later generations, additional horticultural traits were used to select plants for advancement.

Example 2. Mapping of the Male Fertility Restorer Locus

After extensive crossing and evaluation of $F_1$ progeny, two *Capsicum annuum* accessions were identified that can restore male fertility in BCMS lines: 'Flame Fountain' and 'Ganti'. The ability of 'Flame Fountain' and 'Ganti' to restore male fertility in BCMS lines was later validated by remaking the $F_1$ populations. Two $F_2$ populations, BCMS Donor Line 1טFlame Fountain' and BCMS Donor Line 1טGanti', were developed by selfing male fertile lines from these $F_1$ crosses. These $F_2$ populations were used to map QTL associated with male fertility restoration.

Individual $F_2$ plants from both populations were genotyped and evaluated for fertility in the greenhouse. Fertility was determined by the presence or absence of normal anthers and visible pollen in the flowers, although flower formation, fruit set, and presence of seed in the selfed fruit were also noted. QTL Cartographer was used to run a single marker analysis on both mapping populations using the presence or absence of visible pollen to determine whether fertility was restored in individual $F_2$ plants.

The BCMS restorer locus (Rf) from the two *Capsicum annuum* lines mapped to the short arm of chromosome 6 in both populations, between the consensus positions 24.2-32.9 cM (2-LOD interval) in the BCMS Donor Line 1טFlame Fountain' population and the consensus positions 17.2-45 cM (2-LOD interval) in the BCMS Donor Line 1טGanti' population. Rf was found to be completely dominant since the Rf/rf genotype provided male fertility and recombination was suppressed on the short arm of chromosome 6. The Rf locus can be tracked in the population via marker assisted selection by detecting the haplotype associated with the Rf locus (Table 1). Further fine mapping reduced the genomic interval restoring fertility in BCMS lines to a region flanked by M14 and M29. It was determined that markers M18, M19, M20, M21, M22, M23, M24, M25, M26, M27, and M28 are comprised within the region where the restorer factor is located. These markers should therefore comprise a haplotype corresponding to the Rf locus donor line. Markers M14/M15/M16/M17 and M29, which flank the chromosomal interval, may be used to select the recurrent parent allele. Depending on the Rf locus donor line used, M14 may be used if 'Ganti' is used as the Rf locus donor and M15, M16, or M17 may be used if 'Flame Fountain' is used as the Rf locus donor.

TABLE 1

List of markers and favorable alleles at each marker for tracking the Rf locus

| Marker Name | Marker Sequence (SEQ ID NO) | Favorable Allele 'Flame Fountain' | Favorable Allele 'Ganti' | C. annuum Genetic Position (cM) | SNP Public Position CM334v1.55 (bp) | SNP Position in Marker (bp) | SNP Change |
|---|---|---|---|---|---|---|---|
| M1 | 1 | — | G | 17.2 | 213,924,156 | 93 | A/G |
| M2 | 2 | — | T | 17.2 | 213,907,080 | 243 | C/T |
| M3 | 3 | — | G | 17.9 | 213,907,920 | 2353 | A/G |
| M4 | 4 | — | C | 18.8 | 427,239 | 216 | T/C |
| M5 | 5 | G | G | 19.1 | 428,143 | 287 | A/G |
| M6 | 6 | — | C | 20.8 | 87,022 | 117 | T/C |
| M7 | 7 | T | T | 20.8 | 125,861 | 93 | C/T |
| M8 | 8 | T | C | 20.8 | 89,795 | 484 | C/T |
| M9 | 9 | C | C | 21.8 | 386,489 | 313 | T/C |
| M10 | 10 | A | A | 22.8 | 26,405 | 1149 | C/A |
| M11 | 11 | G | — | 24.2 | 3,055,268 | 188 | A/G |
| M12 | 12 | A | C | 24.2 | 3,009,771 | 387 | A/C |
| M13 | 13 | T | C | 24.9 | 2,999,718 | 330 | C/T |
| M14 | 14 | T | G | 25.7 | 3,504,248 | 294 | G/T |
| M15 | 15 | A | — | 25.7 | 3,500,133 | 41 | C/A |
| M16 | 16 | G | — | 25.7 | 3,505,583 | 98 | A/G |
| M17 | 17 | T | — | 26.3 | 3,308,938 | 523 | C/T |
| M18 | 18 | G | A | 26.4 | 3,475,770 | 779 | A/G |
| M19 | 19 | T | G | 26.4 | 3,422,765 | 592 | G/T |
| M20 | 20 | A | T | 30.2 | 4,276,008 | 279 | A/T |
| M21 | 21 | A | A | 30.2 | 4,240,789 | 534 | G/A |
| M22 | 22 | C | C | 30.2 | 4,245,699 | 279 | G/C |
| M23 | 23 | — | G | 31.8 | 70,994,266 | 49 | A/G |
| M24 | 24 | T | T | 32.4 | 4,240,551 | 287 | A/T |
| M25 | 25 | A | — | 34.7 | 6,240,565 | 275 | G/A |
| M26 | 26 | T | — | 34.7 | 6,241,544 | 30 | C/T |
| M27 | 27 | — | G | 35.0 | 8,522,176 | 1140 | T/G |
| M28 | 28 | G | G | 35.0 | 9,799,932 | 182 | A/G |
| M29 | 29 | T | T | 40.8 | 10,670,362 | 246 | C/T |
| M30 | 30 | C | C | 40.8 | 10,664,163 | 33 | T/C |

TABLE 1-continued

List of markers and favorable alleles at each marker for tracking the Rf locus

| Marker Name | Marker Sequence (SEQ ID NO) | Favorable Allele 'Flame Fountain' | Favorable Allele 'Ganti' | C. annuum Genetic Position (cM) | SNP Public Position CM334v1.55 (bp) | SNP Position in Marker (bp) | SNP Change |
|---|---|---|---|---|---|---|---|
| M31 | 31 | T | T | 42.2 | 10,664,630 | 142 | G/T |
| M32 | 32 | C | C | 43.0 | 11,108,817 | 1613 | T/C |
| M33 | 33 | C | T | 44.0 | 11,592,142 | 146 | C/T |
| M34 | 34 | — | C | 48.9 | 21,133,217 | 285 | G/C |

In addition, to have uniform female fertile flowers, BCMS plants should have the Good Flowering (Gf) locus, which is a dominant *Capsicum baccatum* allele flanked by marker sequence SEQ ID NO: 35 and marker sequence SEQ ID NO: 36 on the short arm of chromosome 6. The Gf locus can be introgressed into BCMS plants from any *Capsicum baccatum* line and detected by using markers that flank the Gf locus (Table 2).

TABLE 2

Flanking markers and favorable alleles at each marker for tracking the Gf locus

| Marker Sequence (SEQ ID NO) | Favorable Allele | C. annuum Genetic Position (cM) | SNP Public Position CM334v1.55 (bp) | SNP Position in Marker | SNP Change |
|---|---|---|---|---|---|
| 35 | G | 1.9 | 3,064,350 | 358 | A/G |
| 36 | G | 35.7 | 21,133,217 | 285 | C/G |

The identification of the Gf locus and genetic markers associated with the locus is described in U.S. Provisional Appln. Ser. No. 62/690,722, filed concurrently herewith, the disclosure of which is incorporated herein by reference in its entirety.

$F_1$ progeny from the crosses BCMS Donor Line 1×'Flame Fountain' and BCMS Donor Line 1×'Ganti' have genotypic segregation of ½(S)Gfrf/gfRf+½(S)gfrf/gfRf and phenotypic segregation of ½ completely fertile+½ completely sterile. This segregation occurs in the $F_1$ because the plants of BCMS Donor Line 1 (or any other BCMS line) that have female fertile flowers to facilitate crossing have the heterozygous genotype ½(S)Gfrf/gfrf. The $F_2$ progeny are created by selfing $F_1$ plants with complete fertile flowers, (S)Gfrf/gfRf. Thus, the expected genotypic segregation in the $F_2$ progeny would be ¼(S)Gfrf/Gfrf+½(S)Gfrf/gfRf+¼(S)gfRf/gfRf and the expected phenotypic segregation would be ¼ male sterile+½ complete fertile+¼ complete sterile. However, the observed genotypic segregation in the $F_2$ progeny is ½(S)Gfrf/Gfrf+½(S)Gfrf/gfRf and the observed phenotypic segregation is ½ male sterile+½ completely fertile. The completely sterile plants are missing from the $F_2$ progeny both phenotypically and genotypically, indicating that the gfRf genotype is not transmissible via pollen (male gamete) from BCMS plants. The $F_2$ progeny in both mapping populations had normal germination rates of 92% which suggests that the underlying failure of gfRf transmission occurs early in the reproductive process, before seed formation.

Example 3. Genetic Model of the Male Fertility Restorer Locus for BCMS

There is a dominant nuclear allele present in some *Capsicum annuum* accessions, such as "Flame Fountain" and "Ganti", that restores male fertility in the presence of the *Capsicum baccatum* cytoplasm. The dominant *Capsicum annuum* allele is denoted as Rf, and the recessive allele is denoted as rf. Gf functions upstream of Rf, such that the gfgf genotype masks the male fertility restoration effect of Rf (i.e. recessive epistasis). This is consistent with the observation, represented by formula (I) below, where (S) denotes a *Capsicum baccatum* cytoplasm and (N) denotes a *Capsicum annuum* cytoplasm, that restored $F_1$ progeny from the BCMS Donor Line 1×'Flame Fountain' and BCMS Donor Line 1×'Ganti' crosses segregate for 50% completely fertile flowers and 50% completely sterile flowers, even though all of the $F_1$ progeny are heterozygous at the Rf locus:

Parental cross: BCMS Donor Line 1: (S)Gfrf/gfrf×
'Flame Fountain' (N)gfRf/gfRf→$F_1$:½(S)Gfrf/
gfRf (completely fertile)+½(S)gfrf/gfRf(com-
pletely sterile)                                              (I)

Example 4. Utilization of Uniform Female Fertility and the Male Fertility Restorer Locus for BCMS to Produce Hybrid Pepper Plants Gf and Rf are tightly linked in repulsion on the short arm of chromosome 6. Therefore, the gametes Gfrf (*Capsicum baccatum* haplotype), gfrf (*Capsicum annuum* non-restorer haplotype), and gfRf (*Capsicum annuum* restorer haplotype) exist, but the recombinant gamete GfRf does not exist and cannot be recovered readily in segregating populations. Furthermore, the gfRf gamete is not pollen transmissible from plants that have the *Capsicum baccatum* cytoplasm, as these gametes are generally not viable. This is consistent with the observation, represented in FIG. 3, where (S) denotes a *Capsicum baccatum* cytoplasm and (N) denotes a *Capsicum annuum* cytoplasm, that $F_n$ progeny derived from restored $F_1$ plants (e.g. BCMS Donor Line 1×'Flame Fountain') segregate for 50% completely fertile and 50% male sterile plants.

Under this genetic model, the possible genotypic combinations and associated flowering phenotypes that can be observed are shown in FIG. 1.

Using the genetic model of BCMS described herein, it is possible to design a breeding system that allows easier production of pepper hybrids. In the female pool, the breeder maintains two types of germplasm: an "A-line", which is a line that carries the *Baccatum* CMS trait and a "B-line", which is in the same breeding pool as the A-line, but comprises *Capsicum annuum* cytoplasm. The B-line is the backcross parent for the A-line. The male pool contains *Capsicum annuum* germplasm lines that are homozygous for the Rf allele. Fully fertile hybrids may be produced by crossing the A-line as the female parent and the C-line as male parent (FIG. 2). Due to the male sterile nature of the A-line, it is possible to produce hybrids that do not contain off-types due to selfings. Furthermore, labor is reduced because the female plants do not need to be emasculated.

What is claimed is:

1. A *Capsicum annuum* plant comprising a *Capsicum baccatum* cytoplasm, wherein said plant comprises a chromosomal segment on chromosome 6 that confers male fertility in a male sterile *Capsicum annuum* plant comprising a *Capsicum baccatum* cytoplasm relative to a plant lacking said chromosomal segment, wherein said chromosomal segment comprises Marker M18 (SEQ ID NO: 18), Marker M19 (SEQ ID NO: 19), Marker M20 (SEQ ID NO: 20), Marker M21 (SEQ ID NO: 21), Marker M22 (SEQ ID NO: 22), Marker M23 (SEQ ID NO: 23), Marker M24 (SEQ ID NO: 24), Marker M25 (SEQ ID NO: 25), Marker M26 (SEQ ID NO: 26), Marker M27 (SEQ ID NO: 27) or Marker M28 (SEQ ID NO: 28) on chromosome 6.

2. The plant of claim 1, wherein the chromosomal segment is further defined as:
   (a) flanked by Marker M29 (SEQ ID NO: 29) and a marker selected from the group consisting of Marker M14 (SEQ ID NO: 14), Marker M15 (SEQ ID NO: 15), Marker M16 (SEQ ID NO: 16), and Marker M17 (SEQ ID NO: 17) in said plant; or
   (b) located between 26,405 bp and 213,924,156 bp on chromosome 6 of public pepper genome sequence Pepper CM334 v.1.55.

3. The plant of claim 1, wherein said chromosomal segment comprises:
   (a) the haplotype of variety Ganti, wherein a representative sample of seed of said variety has been deposited under NCIMB accession number 43055; or
   (b) the haplotype of variety Flame Fountain, wherein a representative sample of seed of said variety has been deposited under NCIMB accession number 43054.

4. A seed that produces the plant of claim 1.

5. A plant part of the plant of claim 1.

6. The plant part of claim 5, wherein the plant part is a cell, a seed, a root, a stem, a leaf, a flower, a fruit, or pollen.

7. The plant of claim 1, wherein the plant is a sweet pepper variety.

8. The plant of claim 1, wherein the plant has a blocky type fruit shape.

9. The plant of claim 1, wherein said plant further comprises a chromosomal segment from *Capsicum baccatum* on chromosome 6 that confers uniform female fertility in a male sterile *Capsicum annuum* plant comprising a *Capsicum baccatum* cytoplasm relative to a plant lacking said chromosomal segment, wherein said chromosomal segment from *Capsicum baccatum* is flanked by Marker A12 (SEQ ID NO: 35) and Marker A35 (SEQ ID NO: 36) in said plant.

10. A method for producing a *Capsicum annuum* plant that confers male fertility in a male sterile *Capsicum annuum* plant comprising a *Capsicum baccatum* cytoplasm, comprising introgressing into said plant a chromosomal segment on chromosome 6 that confers male fertility in a male sterile *Capsicum annuum* plant comprising a *Capsicum baccatum* cytoplasm relative to a plant lacking said chromosomal segment, wherein said chromosomal segment is flanked by Marker M29 (SEQ ID NO: 29) and a marker selected from the group consisting of Marker M14 (SEQ ID NO: 14), Marker M15 (SEQ ID NO: 15), Marker M16 (SEQ ID NO: 16), and Marker M17 (SEQ ID NO: 17).

11. The method of claim 10, wherein said introgressing comprises:
   a) crossing a plant comprising said chromosomal segment with itself or with a second *Capsicum annuum* plant of a different genotype to produce one or more progeny plants; and
   b) selecting a progeny plant comprising said chromosomal segment.

12. The method of claim 11, wherein the progeny plant is an $F_2$-$F_6$ progeny plant wherein said progeny plant comprises said chromosomal segment.

13. The method of claim 11, wherein said crossing comprises backcrossing.

14. The method of claim 13, wherein said backcrossing comprises from 2-7 generations of backcrosses.

15. A *Capsicum annuum* plant produced by the method of claim 10, wherein said plant comprises said chromosomal segment.

16. A method of producing food or feed comprising obtaining a plant according to claim 1 or 15, or a part thereof, and producing said food or feed from said plant or part thereof.

17. A *Capsicum annuum* plant obtainable by a method comprising the step of introgressing into a plant a male fertility restoration locus allele for *Baccatum* cytoplasmic male sterility, wherein said male fertility restoration locus allele is defined as located in a chromosomal segment on chromosome 6 flanked by Marker M29 (SEQ ID NO: 29) and a marker selected from the group consisting of Marker M14 (SEQ ID NO: 14), Marker M15 (SEQ ID NO: 15), Marker M16 (SEQ ID NO: 16), and Marker M17 (SEQ ID NO: 17).

18. The *Capsicum annuum* plant of claim 17, wherein said introgressing comprises backcros sing or marker-assisted selection.

* * * * *

SEQUENCE LISTING

<160> NUMBER OF SEQ ID NOS: 36

<210> SEQ ID NO 1
<211> LENGTH: 434
<212> TYPE: DNA
<213> ORGANISM: Capsicum annuum

<400> SEQUENCE: 1

| | | |
|---|---|---|
| gagtcagatg gacgcgagct gaggatagag tatagtttcc tcaggaaagt agctggtgtg | 60 |
| ccaacgagat tcaagctgaa agagatcgaa gaagcaacag ataattttgg ggcgttggtt | 120 |
| ggccgtggat cttccgctag cgttttcaaa ggcgtgctga gcgatggtgc agcggtggcg | 180 |
| gtgaagagga tcgagggaga ggagcgcgga gataaggagt tcaaatctga agttgctgca | 240 |
| attgctagtg ttcagcatgt taatcttgtg aggttacttg gttactgtag tgttgttccg | 300 |
| tcaggaccga gattttttggt ttatgagtat attttttaatg gatcgctcga taagtggatt | 360 |
| tttcggagga ggggtatacg aggctgtttg tcgttggatt tgaggtatag agttgcggtg | 420 |
| gatgtggcga aggc | 434 |

<210> SEQ ID NO 2
<211> LENGTH: 461
<212> TYPE: DNA
<213> ORGANISM: Capsicum annuum

<400> SEQUENCE: 2

| | | |
|---|---|---|
| ttgattgcac tctgaaaagt tgcagacaag ttatgaaata aaagttccat tagctgacat | 60 |
| gcgattgtat catcccagtc agcgtgttgt aaggtttcca ctccttgttt ctcattggac | 120 |
| tgatgacact tgccttcaag tgaacggacc tcgttagatg tgcttcgaag ttttcatct | 180 |
| aatagctcat atctcggaaa ttctgtgagg acagagaag gtgtatcaat aggaacatct | 240 |
| agtggaaact cggataagaa cttcctcttg ttcctactac cttttttcctg tgctgaagtt | 300 |
| gtcaacgact tctcactggc accatcactg ctgctatgat cacccacgtt cattatcttt | 360 |
| tcaatggtca gtagacgttc tgcagtggag ataagtattt accgtacaaa aggttactgc | 420 |
| tactagcgag tcccgaaata gtatgagttg atattacgaa a | 461 |

<210> SEQ ID NO 3
<211> LENGTH: 2458
<212> TYPE: DNA
<213> ORGANISM: Capsicum annuum

<400> SEQUENCE: 3

| | | |
|---|---|---|
| gaagattggt tcagtggctt ataagctctc acttccccat acgtcttttt ttttttttgg | 60 |
| gatacggatt ttattcaaag agtaccaagg tggtagaaca aaaggtacat gacttagcaa | 120 |
| caaactctat aatccactac cacatattat ctcctagcaa gtacaaaagg ttcaaatact | 180 |
| tatccatcat atctaaagtg ctgctataac accaaaagta cagattttttt atacatttat | 240 |
| ttttttactct agaaatgttt aacttcttcc catgaaagca tgacttgttt tctagccata | 300 |
| aggttcatat tatgcaattg ataatagttc tccgcattgg cttcaagcta cttcccccta | 360 |
| ggttgttgct tcaccaacca tttcatgtat ccctgttgaa gccttgctat gttgttccag | 420 |
| gcgtcattac acatcctcca gtagtggaca ttttcagtcc ttactgtccc aaacctgagt | 480 |
| aggtgttaga caagaggatg atccaaagag gcaataaggc cattgctcac gtgttcattc | 540 |
| agtgggagca cattcctgta gatcaggcta cgtgggagga cttcaatgca atcaagactc | 600 |
| gattctctttt gtttgttcct tgaggacgag aaagttttta atggaggagc attaatgtgt | 660 |

```
tctggaatcg agaagcagaa ttatgcagaa aaaggtggta cgctaagttg gaggaggtgt    720
acttagtggt ctgcccatta gttattacgg ttaagcaaga gaaggcgtgg tgagagtgac    780
aaaaggccta atctgtctcc taagtggctc agggtcaatt cttgctagga atattccacc    840
ttctggtatt acattgggta tgctgttgtc gttttgctgt cattacagtt tttccccctt    900
acttttcaaa cacgggttag gttaatcgcg cattagccca tcttattggg cacttttgct    960
ccaattcctt tttggcatgt tcactcgtat atgtagttgc agagttccca ttcagactta   1020
tgaatcaaaa cccgtagcta tttccttctt cttttgtagt tagcttatta atccttcatc   1080
aattgctccg ttccaagctc gattgcatca aaactactgg aagttacaag taaatcagca   1140
gacattatga ttaaattcat tcatggccta aaaacctact agcttatgta aaaaaggtac   1200
gccatatata ctaacaatat ctgtaaacag ttacgacatc aatcaagcag gcgaagaaat   1260
tttattccta caaattcata ccttaaactg gttctggcgt tttctggctt tctctagttc   1320
ctgctcgaga tgagctgctt ctcgtttcaa ggttgagaaa tcttcctgca gtgagccctt   1380
ctccatctcc cgtgcttgac acttcttcag tatctcttgc tccctcgcaa cagcttggtg   1440
gaagtttgta gcagacccca gggcagccag cgttgcagcc tccaactctt tctttagcac   1500
agcattctcc acctcaagtc tgtgaagagt agagttagcc atctcaattt ggccgccggc   1560
atttgacaat gcatacccca tttcggagag cctcttcatg ttgcattctc cctgactttg   1620
cttttccttc tgaattttct cagcctcttc tttctcttgc cttagcattt taagctcccc   1680
ctggtccttg ccaagcctcc gagcagcctg cataaccttc tcattggccc aatcagtcca   1740
cccttggagc tctttctgca gtgtctgcat acgagaaatt agcaacaata tagtttcgtc   1800
tttctcattt tgtgggacat gttttccccaa agactcatcg tatgggatac cagtataata   1860
gtctagaaat ttaggagggg caggaatgct gcctggggcc tttgaggaag acttgggctc   1920
cggaactaga gatgcaggag tatttgtgtt aacagcaggc aacgcacaaa cagtatcttg   1980
ggtcgctggc ccactaccag tttcacttga aggtgcaacg gaggaggagg tgcatgaact   2040
atgagaacag cctccggcta aagggccatt gcttttaact gtattcgcta ccttagagta   2100
agtactcttc attacgagac cagaagaaca agattcagag ctcagcgtct tgtccaaaac   2160
catattgctc caggtggtga gttttgcttt aaaggaaccc ttactcatac gacctctata   2220
gcttttctcg aaatgaaacg tcttttgcct aagcatatct ttcttggagt tcagagacga   2280 tcccctttctc ccgttccac cttttttcttc taaaattgca gcttttgtta tagacagtat   2340
actctccccg ctgaccctg cagacttgct cttcgctact ggaagacgag ctgaacttct   2400
ctttgctgta atttccactt catgaagatg tgagcatata gaattagaca attgaacg     2458
```

<210> SEQ ID NO 4
<211> LENGTH: 829
<212> TYPE: DNA
<213> ORGANISM: Capsicum annuum

<400> SEQUENCE: 4

```
tttactgaaa tatcggtatg tctaatagaa atttgagtac aaaggttttg agtcttagtg     60
gtgatgcatt gtcattctcg cgcattcact gataaagctg cattcttttc atataattat    120
cagggtggaa aatcgtcgag agttgtcaac tgtgttttgg gacttaaagc ctacggcgag    180
tggaagcaga caggtgggcc tggagtctgg aaattcggtg gaaatgtgaa atctacaaca    240
tcagcaaaac aattcgtgcg caaaaattct gagccattct caagttctct gtcaaggagt    300
```

-continued

```
atgtcgatga atgagaaatc tgcaaatggc gtatgcactg acgctgaaag taacaaaatg      360
gtaggtagac tctgcttgac gaacatttca tgcatcacca ataacggttc aatggcatga      420
ttcatcgatt aaatcttctc tttcacagtc cagctcttcg ttgagcaacc ttgttcgtgc      480
aattctgatt gataagaagc ctgaagaagt tccgaatgta agttgaaatt cagtaaattt      540
cttgctgtat tcagataaat tttccgtcta gattcttgta gttgcaaaag aaacacttgt      600
ccaagcgtca agtttctcgt tccctgcatc attttcaaga gagttacttt gtattttcgc      660
tatttagcca aagtagagag agggaccaaa ctataaggcg aacttaaaat tagtagggaa      720
gaagtaaaaa ctcaccgggg taaactgtga tcaagccgtc tgccactaca gtgcatcgta      780
ttttggtatc tagtgccgtt gttctaagat acagcaatgt tgtacttgc                829
```

<210> SEQ ID NO 5
<211> LENGTH: 400
<212> TYPE: DNA
<213> ORGANISM: Capsicum annuum

<400> SEQUENCE: 5

```
gcttgtggaa tcagttctga ataaggtcgt tgaggagttt gagcagcgca ttacaagcca       60
aatacaactg gtaagtttag cttctccgcc ttgttgcatt tgttttcatc tttcgtcttc      120
ttctctgaca ctgcattcac ataacattct atcagaacaa agcaactcca aaggactcaa      180
cagtttccag cggcaacaag ttccttcaga aacatgcgtc agtcagcgca aaggtaatgc      240
ctctgatttt tgcaaatcat aaggtactta ttcatgtaaa tagagggtca ctcatactag      300
tgcctttttt tgttcttgtt ctctttctca attaggttga ccaaagaaat ttagcactag      360
tgaaagaaga gaatcgcatc gtcaatgagg aacttaaaag                            400
```

<210> SEQ ID NO 6
<211> LENGTH: 459
<212> TYPE: DNA
<213> ORGANISM: Capsicum annuum
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (365)..(365)
<223> OTHER INFORMATION: n is a, c, g, or t
<220> FEATURE:
<221> NAME/KEY: misc_feature
<222> LOCATION: (374)..(374)
<223> OTHER INFORMATION: n is a, c, g, or t
<220> FEATURE:
<221> NAME/KEY: misc_feature
<222> LOCATION: (376)..(376)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t

<400> SEQUENCE: 6

```
cttttctttt ttagttactg gttgaactat ncgtgtgcga gttttttatc tgaactatca      60
ctaatttatc aaaatatgtc ttaattatta aggagtcgtt tagtagncgg ttaaagctat     120
gctggtatta ctaatgcatg gattggttgt gatttatgaa cgaatttatg tattatttta    180
tgtaggaatt agttatgcng attttttgtta tttacttaca tttttcatgt ataacgtatt   240
tngccttcta tcgtgnagga aatagtacat agatttgttt ataacttatg catatattag   300
ttagttatgt taattttttta tttataaatc aaatattata tctatttata catgaataac   360
ttatnttttta tccncnttgt ataantagtt taatagtaca taaataacat gtctcattct   420
caattaataa ttgtttaaat taggtgtgcc cttcaagat                             459
```

<210> SEQ ID NO 7
<211> LENGTH: 429
<212> TYPE: DNA
<213> ORGANISM: Capsicum annuum

<400> SEQUENCE: 7

```
tgggggaatt ttgttaaaag gattctgggt cacataatct caagccatga tgtggatggt      60
ttgctgactc aaccagatgg tactagcata aatttgaaca tcaaggttgg tttagtccac     120
ctcaaaaagt taactcataa aatcttttta actaacacga gaagctcatt ttcttttctg    180
gctcttgaat tgcagaaggg ttctcaacac atgtgtgtag aatctcccgg agtgcatgaa    240
ctgagctttc caaattcatg tgtttcgttt gggagttcat ctgtggttat tgacacatct   300
aacctttctg tatgatcctt taggagttga attcttccat tctactatttt catttatcat  360
gcatgtcttc tcatttattt tcttctgttt gtagcctatc tatttgaaag gcgagagcta   420
tcttttttga                                                              429
```

<210> SEQ ID NO 8
<211> LENGTH: 1348
<212> TYPE: DNA
<213> ORGANISM: Capsicum annuum

<400> SEQUENCE: 8

```
caattctcta agcagatgat ataagttatt cattcctaac tcaagtatgt tgctcgatgg      60
atgagggtca acctgtattt atttttgaat tccgcagaat ctgctttccc tagaccatac    120
aacttaagaa gttgcgggga gggagggcta tgagagttgg ttccgtttta tggaatttttt   180
gtaacctgtc cttctactgt attcttgtta actaaagagt gttgctcggt tctgctgcag    240
gcttttaatg gtggcgaatg ccggagactg tcgagcagtc cttttgccaca agggtgaagc  300
agttaatatg tctcaagacc atagaccgaa ttatgcatcg gagagaaggc gtgttgaaga   360
gttgggtgga tttattgacg atggttatct caatggtgtc ctatcagtga ctagggcctt   420
aggagactgg gacatgaagc tgcctcgtgg ctcttcctct cctctgatcg cggaacctga   480
attycgacag atcatcttga acgaggatga tgaattcctt atcataggtt gtgatgggat   540
ctgggatgtt atgtcaagtc aacaagctgt taatcttgta cgccgtggtc tgaagcggca   600
tgatgatcct gaacagtgtg ccaaggacat tgtcatggag gccttgcgtc tgaacacctt   660
cgacaatctt actgtggtaa tcgtttgctt tacttcccctt gatcatcctg aaccatcaca   720
gtcgcgacaa aggcgattaa gatgctgcag cttctcagcc gaagctttgt gcagcttaca   780
```

```
gagttggttg ataacagtg gaaaccgttg agttttcgt acatacaatt agttgccgga      840
gaggatgggc gcggtgtttg ttgtatggca gtctctcatt ttattagctg tacataacaa      900
ctactttcaa acttaaattc atcaattgaa atattttgt caaagttgtt tgggtaacag      960
gctgaaatgt gtgggtacta actgttctg tggttgtcga agctaccagt cgcatgaagc     1020
tatgaaatga gacaaccggg ctatagctac cgtaccacca gttagtcttc ttcctcctcc     1080
ggttcttggg aacttgaagg taagttcagt tttattggta taactaggtg tctgcagagc     1140
tcacgtcaat atttccatcg atatatact catcatcatc ttgtcgattt caaaattta      1200 ccttatctgc tacaagaagc gttaccaaac acttgatcat gacgaccaca acgttattgg     1260
tatgagtact gctgctaagt tgctggtgtg ggattcaacc agcgcggctc ttggctacgc     1320
gttttgtata tatcctttgt tgtcctct                                       1348

<210> SEQ ID NO 9
<211> LENGTH: 451
<212> TYPE: DNA
<213> ORGANISM: Capsicum annuum
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (224)..(224)
<223> OTHER INFORMATION: n is a, c, g, or t
<220> FEATURE:
<221> NAME/KEY: misc_feature
<222> LOCATION: (272)..(272)
<223> OTHER INFORMATION: n is a, c, g, or t
<220> FEATURE:
<221> NAME/KEY: misc_feature
<222> LOCATION: (401)..(401)
<223> OTHER INFORMATION: n is a, c, g, or t

<400> SEQUENCE: 9
ggtgactgac attgttgtcg agctttggtg gtatatgaac caactattgg aatccctcca       60
gaaactttgg tcatcaattt gaagaccttg ttagcttgta aaacggtttc tttgagtctc      120
aatgggttga acagtatat tcaccaaatt atatttggtt tgaaacaaac ctcatagagt      180
tggtccatat ttncagatga atacttagaa ttgggccgat gttngagact atattgaaac      240
tttcctagct cttgaaggga ttgaaacact tnccgtgatc tcttgtgtga ggaaaagagt      300
gatgagtgtt cgcgcaattt gaatgtgttt tagccttatc ttcagcttgt tagctatctt      360
ttcaatctcc attgaagata gaaactcggt taactttgtc ntagaggaac agttgtgaat      420
atgctctcat aaagacaatt ttagatccat t                                    451

<210> SEQ ID NO 10
<211> LENGTH: 2160
<212> TYPE: DNA
<213> ORGANISM: Capsicum annuum

<400> SEQUENCE: 10
gattgcattg atgcaagctg ttcacgagcc ccttgtgcct caagttttgc actcaaaagc       60
tcttggtaaa gctaaagcat taaaatataa gtcattgcac tgtagtactt acaggaaagg      120
tataatggat atcaaatgta aggtcaaat gtaaaaatag atcctagtag tcaaagaata      180
ggcttgaaaa catgctcata acaatgcaga ataacaccaa tttctttggc ttatttgact      240
ggcaggatca tttgagtatg tatccaatag agacatgcta tacccactca actcgaaagc      300
tgtgaccaac ataatgtatt ttatgaatca cttacggagt aatgccttgt actgtatgga      360
```

| | |
|---|---|
| atatggtaca aggaacagga catcacaggc aaactcaaca acaaaacaa aaggccaaaa | 420 |
| cttgattctc actctgagat gtggcacgtg cagaggaaac agatgtgata agatgtgagg | 480 |
| taagaaagag gggaatgaga gacatatctg tgcctaaatt gtagaaggaa agcaaaatac | 540 |
| catttaaagc ttcatttaat aaatgaaact aataactatt gaataaataa aatcaccatc | 600 |
| agttacgtca ttctaattgt agtcactaca aaagttttg agaatgtatc ttgggactaa | 660 |
| gtttaagaat atgatcttcg accaccaagg cttatatcct aggggtacca ctgtggatct | 720 |
| cctacacata aggtttggaa tcaaatcttt ctatcctctt ccccttcccc ttcccttgtc | 780 |
| cctctatgta acaaatgaaa ttaaaagaat gaaaaagtgt gactaaggca taacggaagc | 840 |
| ataggaatta attaatcaaa acaaatatgg atcttcaaat tcagattcag cattggcatg | 900 |
| ttttggcatt tgagctcttt aggtggcttc tcctcttcat tactagttag attttgaaag | 960 |
| cagtacttag taatgacatg cctacttcat ttataaactg gaaaattact aatcacgcaa | 1020 |
| cacttattac tatatctata aagaataccg catgtttcat atttcctggt gcattcatca | 1080 |
| tgcaagtggg agagaaacag aactttatta gtattctatc agttagaaat agcagatttt | 1140 |
| ctagtaacag ctctcactag ctgcttggtt gtgagaatac aatgataggg atagatatat | 1200 |
| acagtcacaa tatttatgct accattagag aaattctgaa gtgaccaagt gtatatcacc | 1260 |
| actttgtttg ctctcttgat ataaggagat aaattatcat aattgcaact ttcaatgcat | 1320 |
| aaaatgtgaa agactgatta cctcttcatg cttctctctt gcagatatgg tctgctcagt | 1380 |
| tgctatctca acaactgagt ccaaattctg ttggcttgag gatctctcca tttctaacat | 1440 |
| agtgacctgc acaaaagctc cacatttccg agaaacactt aaaaagcaga aagtgacaa | 1500 |
| ggcaatcaat cttattcata tagatgccag gaaaatgaga aagaaagaa atgaggacac | 1560 |
| cttctcttgg agctgcttaa tcaccaaaat agcttttgct tctctcaaag gtttgctccc | 1620 |
| acacaagtgc atcaaagagt tatcctcttg ctcagaacca tcgaccagat gaatgtcagc | 1680 |
| ctcaaaaagc ttccttgtga gatagtcaat ctttacctca ctcacggttt tctagcaaaa | 1740 |
| gcaaggatta aactaagaaa tcaaactgaa tcagaaataa cagaaggaag caaaagactg | 1800 |
| ttacatgtga ttcatatttt aaaagcaact cttcatacac cctttgaagt tccaggaaat | 1860 |
| cactgtcttc ctgccaaaat taaaaaataa taacacaaca gtggtataat acaattttga | 1920 |
| aagaaagctg aaatagcagc gcgaagtgtg aaccattgag aagcttttttt tcctagaggc | 1980 |
| tccttttctc ctgctagtga catgcaacaa agcccgcggg tcagggagag tacagtcttc | 2040 |
| agcttgatta ctccttgcat tgtcttcttg cttgccagag tctaaattga tgtcaacatc | 2100 |
| taatagttct tcaaaaggaa gtaagggtcc aatgtcacgt tcaagccttt tggctttgac | 2160 |

<210> SEQ ID NO 11
<211> LENGTH: 493
<212> TYPE: DNA
<213> ORGANISM: Capsicum annuum

<400> SEQUENCE: 11

| | |
|---|---|
| accgtgaggg atgcttttgt atatactgta aagccagtct taagtccaaa tatctgaagt | 60 |
| tggtttcgcg acttgctatg cttattgttt ccaagtaatt ttgttctgaa tggttgtttt | 120 |
| tagtgttgta atttgtaaat gatgatatgt atgttcttct acagaccgaa agttctggag | 180 |
| gttcaccgga gcaggatttt gtccagaagg catttgagat tcatgacaag tatatggtgt | 240 |
| atgtgaaagg ctgttttgct gataacacta tctttcacaa ggtattccga ctgttaactg | 300 |

```
ctgtacgctg atcccttta cgatgaatta cttgagacgt tatatagtta tgttcagtgt      360
tgtcgaaggt gcacataaga cctgaatcga ggctcaaatg tgtttgagag tttagcgtcg      420
cttaatgtgc acatattcct ctgaatggtt ctcttaggct gatgtataaa ctctttgact      480
ctcataggct ctg                                                         493

<210> SEQ ID NO 12
<211> LENGTH: 516
<212> TYPE: DNA
<213> ORGANISM: Capsicum annuum

<400> SEQUENCE: 12
tgctattgag gatacattgg ataaggtatg cacaaatttt acatctccga tcaatttggt      60
ggtcgaactt catatctttg ctcaaacatc gtcaaaattg tgtacttttg ttaggtggtc     120
aagcttgtga tgtacatcag cgacaaagat gtgtttgctg agttctacag gttggaattc     180
agtgccagca gttgttttga catctttaac catttgatat gctaactgtc ttaatactta     240
taggaagaag ctttctcgcc gattgctttt tgatagaagt ggcaatgaag aacatgaaag     300
gcttatctta tcaaagctaa aacagcagtg tggtggacag tttacatcca agatggaggg     360
aatggtaagg attgttcaat ggacttmgaa agttttgtct ctttaccgcg cttgagatat     420
ctgaaaacga atgactggaa atgtaaaaca ggtaacagat tgtcattgg tgaaggaaaa      480 tcagactcac ttacaggaat atatcagtaa caaccc                                516

<210> SEQ ID NO 13
<211> LENGTH: 1880
<212> TYPE: DNA
<213> ORGANISM: Capsicum annuum

<400> SEQUENCE: 13
gttccatgta tttctggaaa acagatggta caagggtggg tttaaggaaa gggtaatttg      60
gtaaacaaac attttttac aaaatttata taaatatata ttatctttaa tacatcaaac     120
caaacaatgt gtaaaaacaa atgtatgtgt aactaatact agcattacta ctacttgcat     180
taataataca agcattacaa ataccccccta tttagcatta ttcttataca ctctaccaaa     240
cgacacccta agcactttgg catgtacaaa tactacctac catacgatct ttttaacac      300 aaaactttca tgcttgcaac agttttttgy atgtcgtctc aatgaatgaa ccaagttcaa      360
attaaaatgg gaactcactg gcagagtttt gcagtgctgc tatagattct ccttgactgg     420
ttccgttcac catgcttgga gctgtctaat tctagtaagg aggcaccatg gagaaacttt     480
aatgccgctt ggaaatagat acccgtactt tcacttgatc cagaactctg aaccaaatag     540
ccaaagtcaa cataaaataa ataaatgaaa caaataagaa agcatatcca ccatatttg     600 tccctccttt tcttaggaca aagtgtaaaa ttcttttaac cttgagacga tctgccagat     660
gttttaggtt tgtggcttct tttatggcat ttgtagcagc ttgacttgat gaatccttct     720
gagcagggct gggaacatct tgatccctga ccttattagc agtattatta ggtaggtttc     780
catggtggct tttagctgtt ttaccctgtc ttgaagcatt tgacttttcc ctttcagaag     840
catcaactat aacacaattt gcctcgtttg cccgtccgga tccaggaact ggctctttaa      900
atacaaccgt ctcattctga actcttgtta atggaaactt ggaagagact tcaatctgct      960
cacttctgtt ggaaacaagc ttcttagatg atctctgatc atttcgatct ggtagtgcag     1020
cctggctttt atccaggcgg gatgcaacat ccgatcgagc ttctgcacca tcatgatgac     1080
caactcgtgg ttgattatca ccttttaacat ttttgtccaa taattttcca gatgaatcct     1140
```

```
tcttagaact cttctttaat ctatctgaac caacaacatt ctcctgaaac ttgttttttc   1200
ctggtgccgt cttctcctcg tctaatggca tttgatctga agataaattt aaaatatcag   1260 gattttggt gttacattgg tcagaatcag attctggagc ccgattcttc tctttgcgcc   1320
gtgacaaaga acctctttta ccatttgaga caaactcact atcctgacac tgatagtcat   1380
tctttctctc cttatcagag ccttggtctg agttttctgt cttgcaagaa aattgaccaa   1440
cttgacgtaa tggatcggca tttacatcag catccagatg agttgcataa ccagagacca   1500
tggtctttgc tttaactgtt gtatctgatt cacgatggac atctttctcc tctaaatcag   1560
cttcagctaa cacaacataa ctcgtgccat tgcatgcact atccttctta acaaaactgg   1620
attcatttga aacccatca ttttcaccat cagaagacct cttgggactt gaagtgggaa   1680
cagctgatga ggcagcagca gaaggccgtg aattgcctag atccttttg aagaatctgc   1740 agcttttaca ctctgcaaag atacagtgag atcttgccca gcctgctgtt ccttttaac   1800 tcgacatgtt ccagcactac ctttgcttgc gctagtgtct ttccggtcag acttggagac   1860
ccttgctttc ttttccttcc                                              1880

<210> SEQ ID NO 14
<211> LENGTH: 2286
<212> TYPE: DNA
<213> ORGANISM: Capsicum annuum

<400> SEQUENCE: 14
gttaggggaa gtacaaataa atcagcaagg aaaagacaag tccatttcat attgcagaaa     60
acatgttttc cacttcataa gtaggccatc atagatctat aagggattat tgatcattct    120
agtgatagtg ttcttaaccg ttactaacaa agatgaagga tatgtatagt tcttggtgtt    180
agtatgccca tgagaattgt aagatgggat tttagtttca ctataagctg cattttgtt    240 tcacctgtaa catcttctgc tatctagatt ggacattgtt ttggtctaca gctkatgaac    300
tttgagcagt ggactacgct tgaaatttta aaattatcca ctatgctgat ttttacgcat    360
taccataact aactgcattg cggtgaaaac tcaatgcatg tccttaagcc gtaggttgct    420
ttctaatcag caaacaagtt tggtgaacaa gttctctgaa tctatccatt ggttatcctt    480
gtctcgacaa gctagttctt tttccttttc tattctgttt gaattatatg agtcagcaaa    540
gtatagattt tgaaggagtt caagtaggaa atattaccgc tttggaaatt tacagatttg    600
cttttaaaac tttaattatg tgccacaagt ctagcttttg gaaatattta acatgcttct    660
tgaactgggt ttcataatgg tcaagtgccc atgaatttta ttttttctct tccgctgaat    720
acattatcaa acttcgaact tgaatcttca ttactttgca gacaactaga gtatttgctc    780
cttggctcaa taatgcaagc ttagagaatg aagaatcttg gcatgaaatt gctcgccctc    840
aagttcatgg tcatgacata aattgtgtga cagtaatcaa aggaaaagga aaccatcgtt    900
ttgttggcgg ggctgacgag aaagttgcca gagttttga atctcctcta tccttttctga   960 agacattgag ccatgttact tcagacagct ctagttttc tgccgacatt caagctgatg    1020
tgcagatatt aggggcaaat atgtctgctc taggtctatc gcagaaacct atatatgttc    1080
agggtgagtt ttccagtcta ttgtgtggta tcaatttgc ataataacat ataagatact    1140
cctattcatt tatgtttcca tcatcacttt tgatgttaca gggtgatata taactgagtt    1200
gttgacttgt caaaattaac tgtaaagacc ttctcttaac catgtattga attagaatta    1260
atgtgatgtg ttaccgactc tttctctaag tttgcttaaa gtgctgtgat atctgatgca    1320
```

| | |
|---|---|
| aagtgttctg actttgatac aaacagcgat tatcctgaat atttcgtttg aggactctta | 1380 |
| tatgttataa tatctcatac atctaagcct atcttttgca gcagcatcga caccaacaga | 1440 |
| cagaagcaat acggaaggtt tgatacact agaaactgtt cctgaagcag ttccagttgt | 1500 |
| cttgacagag ccacctattg aagagcagtt ggcatggcat actctatggc ccgagtcgca | 1560 |
| caaactttac ggtcatggga atgagatttt tgctctatgt tgtgatcagg agggaaagct | 1620 |
| tgtagcttca tcctgcaagg ttttctctc tttcccttt ctcctccttt cttttgggtg | 1680 |
| ttggcatggt tcttccttgt ctgtcttgaa tcttctgtta atagcattca acttgattgt | 1740 |
| acttttgcta agtgccctga taaagttggt ttttagtttc tggtcttaat atacttcgat | 1800 |
| agaaaaaaaa ggtagtactc cattccatat atggtgtcaa ttttttttcaa tatcttgacc | 1860 |
| attagacgcc cctatttat tggtggatgg ggttagttaa ggaatagctg ggtttgatcc | 1920 |
| tgcggcattt tctctcttat gagaaatcaa acgccaatct gctcatttta tataacttac | 1980 |
| tggtgatgct cactacctcg acttttacg ttgttagaga cctctatgaa ctatagcaac | 2040 |
| acatgatgga attcacaata ttcttctaga tactcctttc aacttctaat gatttttttg | 2100 |
| ggggaagtct ttattttctt aattagttgt gtctatcaga aacactctct ctacctccga | 2160 |
| ggtaggggtg acgtgtgcgt gcgtacactc tacccttcct agacctcact ttgtgtgatt | 2220 |
| acactggaga tgttttctg ttcttattta attgtgaata ctaattatgc tggggctata | 2280 |
| taatcc | 2286 |

<210> SEQ ID NO 15
<211> LENGTH: 358
<212> TYPE: DNA
<213> ORGANISM: Capsicum annuum

<400> SEQUENCE: 15

| | |
|---|---|
| gattccgtaa tcactctaac ggctgaaata tatctgattt agtgcttttc ggttcattat | 60 |
| aatcagtaat ccagccagta tgggtgacgg tcatgtcaat aatctgaaat gttatctgcc | 120 |
| ttttctgta atactatagt ctatagtatc atttatgtgc accaagagag cgaactaagc | 180 |
| atcaatccac gcagctattt ctgtttaaga atttaggcta agtagatttt tgtgccagta | 240 |
| aatgttttac tcttttagtt tctaagttga aggtgattca ttaattactc ttttagtttt | 300 |
| taggttggag gtaacctcta tgcagattta gttgggttta taaggatgca attatatg | 358 |

<210> SEQ ID NO 16
<211> LENGTH: 1273
<212> TYPE: DNA
<213> ORGANISM: Capsicum annuum
<220> FEATURE:
<221> NAME/KEY: misc_feature
<222> LOCATION: (470)..(470)
<223> OTHER INFORMATION: n is a, c, g, or t

<400> SEQUENCE: 16

| | |
|---|---|
| tgggggcatc tctatggccc gagtcgcaca aactttacgg tcatgggaat gagattttg | 60 |
| ctctatgttg tgatcaggag ggaaagcttg tagcttcgtc ctgcaaggtt tttctctctt | 120 |
| tcccttttct cctcctttct tttgggtgtt ggcatggttc ttccttgtct gtcttgaatc | 180 |
| ttctgttaat agcattcaac ttgattgtac ttttgctaag tgccctgata aagttggttt | 240 |
| ttagtttctg gtcttaatat acttcgatag aaaaaaaagg tagtactcca ttccatatat | 300 |
| ggtgtcaatt ttttcaata tcttgaccat tagacgcccc tatttattg gtggatgggg | 360 |
| ttagttaagg aatagctggg tttgatcctg cggcattttc tctcttatga gaaatcaaac | 420 |

```
gccaatctgc tcattttata taacttactg gtgatgctca ctacctcggn acttttacgt      480
tgttagagac ctctatgaac tatagcaaca catgatggaa ttcacaatat tcttctagat      540
actcctttca acttctaatg attttttttgg gggaagtctt tattttctta attagttgtg      600
tctatcaaaa acactctctc tacctccgag taggggtgca cgtgtgcgtg cgtacactct      660
acccttccaa aacctcattt tgtgtgatta acactgggga tgtttttttct gtttctattt      720 aattgtgaat actaattatg ctggggctat tatatcctgc aggtcaatca ccaccattgt      780
tgaaatatgt tatgggcagt tgggttctgg aaaatcattt ggtcttttgg cattccaaat      840
ttaaaagtga ccccaaggga tttccccatg aaaccaattt ctcttggcct ttaaaaaaac      900 ccctttttttg ttttttaaat taatcaaaag gtttgaacat ttaccaccct cctttgccaa      960
aaattttaaa aaatacaaaa ccaaaaattt ttttttccccc accccaatgt ttatatatac     1020
tgttaatata aaacttttct cccttttgga agtttttttt agaaaaaccct ttctactttg     1080 gagagggaag agcctggcca actcccccccc aaaaccccca cggtgtaaaa ttttattttc     1140
tttcctcccc ccctccacc ccccctcctc taccaccccc ctaaaataat ctccctttttt     1200 ttaatataaa aaacaaaaaa aaaaaaccct cctctttttta acccccttccc cttaaatttt     1260 ttatttcccg cca                                                          1273

<210> SEQ ID NO 17
<211> LENGTH: 1253
<212> TYPE: DNA
<213> ORGANISM: Capsicum annuum

<400> SEQUENCE: 17
gcagaaatta aaatacacag gtaagataag tgggaagcaa catctaattg ggattttttct      60 tttcctttca tatttacaga ttgttttgta tttagacaaa ggagaaaaaa atctaaaaat     120
aacagatagt ggcggagcca cctttgctcc aggggttcat ctgaatccct cgatggaaaa     180
ttttaccgtt tttataatat ttttacatgg ttaaaaatat ttttattcat gtatagtaga     240
tgttgaaccc cgttcgacta gttcgtattt atacttccgt accccctcaa tgaaaaattt     300
ggctccgaca ctgataacag aatgtgatat agacaaacaa caccgtcaga ttttcctcta     360
tttataatgg acttgttgtt atttactgtg caatcaaact aacctttcct ggttagctct     420
tttcatgaaa cttatccaca tgcaagacta cagtacttga aacagataaa agtggtacac     480
ttgtcttagc agatcaacta atgttgcact ctggatacga cttcagtggc gggcttgtta     540
aaacctgcag gaataacatg tgaaatttca aactttcaa gcattcaaca aatatcatct     600
caagtgttga aattccaaag tatatgtcct gaatcttgct ctaatatcca agaaatttaa     660
ataataaaaa aaaactacc ctaggacgat atatgtagtc tgccgatatg atcttcttta     720
gagcagtctt ccaaggatgt gatagggat tgaaatgggg aacatagaag aattgatgaa     780
aaaatttcca agagttcaaa ttatttctac tggtgaggct gttcatagtt cagataagaa     840
gtgtaccaac aatgcaagtt gcagcaatat ctttgctgtg cctgcactca atattgagac     900
atccttcttt cgaatacatc tacgcattca caatgaaccg ataaataaaa gatttgttaa     960
atactgatca ttttcagatc aagattatcg aaagatcact tgaatggttg ttaattttaa    1020
aatggtaaca aaagggagat agcaagtcca tttcatgaaa ctccacaatt acagcgtatt    1080
tgacattgaa aaggcaacat atatgcaatt aaaaaaaaaa agaaatgagt ctacatcttt    1140
tcaaatacaa aagaaaatca aactcaccat ataaagtcta ccaaaagaaa gtgacatagc    1200
```

```
accgaagata tatggactcc ataccaccct ttactctgat aaagaagcag tcc         1253
```

<210> SEQ ID NO 18
<211> LENGTH: 1323
<212> TYPE: DNA
<213> ORGANISM: Capsicum annuum

<400> SEQUENCE: 18

```
ctaaaatttt agcgtatttt tgtcaacctt tttaactgac atagcacctt tttagctaac    60
gtggcacctt tgacgtggcc cccattttta tgtaataaag gtgccacgtc agcacaaaag   120
agtgacaaaa atacgctaaa attgagttcg ggggataata ggaccccgtg aagttggagt   180
gtgtcatagc aactttggtc ataatacaag ggggtacaag atgcttatct cgaagaaaaa   240
tgaaaaatca aagcgcaac gtactttata tgtcagagtg tagcgagtgc acttcaagat   300
gtataataat ttgctcgagg atacagtact aattgaagcg aattacatcg tttcccctat   360
ctatttaata taagaaaggt tttgccgaag aattgggtga aggtgattag acatgacatg   420
acacaacttc aactgaccga ggacatgatc ctatatatga aggcatggag gtcgaggatt   480
agcgtcgaac gttaataggt agacacaagt tgtcatactt ctagtaggat gatttaggta   540
tcacgtagtt tttcccgcct atgttcatta ataactgttg ctatacttgt tttgtgtatt   600
gttttttctgt agtctctctt ttttctctta cttccttgct tttttgcgcc gagggtctat   660
cggaaacaac ctctctaccc cacaaagata gaggtaaggt ctgtttacac tcgatttact   720
gagctcggtc gaggttaagc tgatagctca gaacttgaat gtatattcgt tggtcatart   780
caatctccga accagatcaa cagctccgac accaaggtag ttgagttaag actagcacaa   840
ctttaactaa gctcgcaact tctagtaaag gacgcgtggt tgtgaaacat ggcctgtagg   900
ttctttgttt ttcttttgaat aaccgagaaa tatgttgttt ttatcttcaa aactcggtgg   960
atgtttaagc cccttttctc tatctttctc cgtttaaata ccaaacttaa ttcaccgata  1020
gaatttgagc tcatgatgtg cgcctactac acattcttct tctaacaagc atgcgagtga  1080
caggaaaggg cagtaaggaa acaaagaaga tcatatcaaa agaaaatgtg ggcgaacctg  1140
gttgattcct cggtccttt tccagcaatt ttgcccttgg gagccgctga caactgtaaa  1200
gattagaaca cgggatcttc aactcctctc ctccttgtaa gtaagaagac tagttgtttc  1260
actgtaacta ataatgaaac actaacctgt gaggcaatat cgattccaat ttcatcgagg  1320
acc                                                                1323
```

<210> SEQ ID NO 19
<211> LENGTH: 786
<212> TYPE: DNA
<213> ORGANISM: Capsicum annuum

<400> SEQUENCE: 19

```
actccatttg aactcatctc gttccaatgt tatgtcaata cagataaaag cttccacctt    60
gagtaggggc aattttctga acatatccc ccgctacaaa gtccaaattt tcacttcctt   120
gcagattagc cacgacaggc ggaagatcaa gaacaataca tttcatgtca gggaattttt   180
ttgttatggc cattgcaaca gtaccatttc cctccaaca tccactaaag atgtcaatcc   240
tctgaaaaca tccttaaact cgttgccaat cagtacgtta atgaatgatt gcgaatctct   300
agccatgttc gcgtgaaacc agttaccact actcgtatct ctcgaaagtt tactccagaa   360
taaatctcca tatgctgtgt aaaatgcatt tggatcctca tttctgaacc aatcacctaa   420
acagttcgat ccatgcttta aagaaaaatg aatcttgatc ttccatcaag ttccaaggcc   480
```

```
catccttcat tatatatcgg tcagctagtg caaccgaata ataccctttta ccatcatcac    540 catcgtccac attgttgtct tcatgttttt gtagaatcaa caagccataa ckaactacta    600
ttggtgtaag gcggtgaaag tcgggattat ttgaagggct aatagacagg gaagacatga    660
gttttgatag tgtcattggt tttccttgtt tggttaagtc attaggtatg cctaattgaa    720
gtgcacattt caatgttatg gtaaaagata tgatgaattc aacaaacgtt gacacttatt    780
attttc                                                              786
```

<210> SEQ ID NO 20
<211> LENGTH: 597
<212> TYPE: DNA
<213> ORGANISM: Capsicum annuum

<400> SEQUENCE: 20

```
ggcaaattgg tacttctatc catggaaact attgcagatg ttccataacc aggtagatgt     60
gaagtagatg tttgagaagc aagtgagaag tgtgaactcc tctctcgaac agagggagaa    120
gtgtgtcgtt tatgaatact accatcttcc tcatttatga tctgcacaaa tcacaatagt    180
tccacacttt actccacaac atcggcctta aagactattt cggaaaagat gcccattatc    240
tgtcttggaa ggatgctggc agtaatttat aagagaaawg agagtaccct ttggatagca    300
ggatccaagg acgaaagcaa acgcctagaa cgttctggcc aagttcttgc aaacattctg    360
tacaaaattc ttgcagttga tcggacctgt tgttaaatcc aagggatatg aattgccaac    420
agatcttgaa tcgaattaaa gggggtatac atgcagataa ctatgccaaa atatgatact    480
cagagttcaa caagcatacc tcacccattg catcagagac acaacacttt ataaggtctt    540
catagagctc tgctgaacgt tgtacctcag atgcatcagg ccaatgttca aggatca      597
```

<210> SEQ ID NO 21
<211> LENGTH: 1085
<212> TYPE: DNA
<213> ORGANISM: Capsicum annuum

<400> SEQUENCE: 21

```
ggatccacga acctaataag caccctccat ggatacctcc acaaccgctt cctcccatcc     60
acgcaacaac atgcctagtt caatcgcaca aaagggtct agggagagta gagtatacgc    120
agaccttacc cctaccttgt agagataacc aaaaccctaa acaatggat caaaactcct    180 gtttcatata gcctctaaaa ccccgcttag cccagtttct gccctctga cctctggtcc    240 actgggacct tgcctaccca tagccact tgccaatgga aaactggcta ctcagatgga    300
tgcaagacca atttgataat ggaaaccctca tagcacgaaa ggcaaagttg ttggttatcc    360
taaaaataaa agcgattata ctcaaacgaa aaatgtcatg actgatatct tcataaaaat    420
cttggttcat ttacacattc atagtatact tacaacgaaa gtaataaaaa caaaggtaat    480
atactacctc aacagaaatg gggttgagtt tgagacagtc gaaactacaa tgaattttca    540
ccttcttgct ttcttttata gatttcttaa ctttttaaat gaagatgcac tagatacttg    600
tactaaatag tccaatagca agatgtatca ggagggactt tggtagcaga tctaatctag    660
ctgaggatgc tacattatcg aagttgcaag aggcgctaat acaataacaa cgacacacgt    720
atagcaaatc tggtttctcc gaaagagagg aggagccttg aaacaacgat aaagttgtct    780
ccatggttca agccgtggaa ttaaccgctg atgcttgtta gagtaggctg cctacattac    840
acccctcagt ttgcgaccct actcggacta tgcgtgaatg caggaagctt catgcaccga    900
```

```
actagctttt ttagttctcc ataaacccat acgtcaaaga gaaggcttgt tgagtatcaa      960
agttatcacc acaaatgcaa atggcaattg aatgcaatgc accatcacca gcaaaagaat     1020
agacaagcga caaccaaata cggcagcata aaacaccaag gcaataaact tcaatctaca     1080
gttgc                                                                  1085
```

<210> SEQ ID NO 22
<211> LENGTH: 756
<212> TYPE: DNA
<213> ORGANISM: Capsicum annuum
<220> FEATURE:
<221> NAME/KEY: misc_feature
<222> LOCATION: (756)..(756)
<223> OTHER INFORMATION: n is a, c, g, or t

<400> SEQUENCE: 22

```
gatgatgtcc acaggatgca gcatggtccc tatgatgtat cctggattcc cgcaatatat       60
gccaacaatg ggaatgaaca tggggatggg gatgagtatg gaaatgggca tgaatcggcc      120
aatagttcct tatcagccgt taatgccaag tccagcaatg cagaatgcag ctgcagtagc      180
acaaatggct cctagatatc ctcttccggc atatcatttg ccaccatttc ttgcacctga      240
ttcatccaga atccctgttg cgaatcagcc agatcctccg aggctaaact cacttgttgg      300
acataatacc aatcagccaa aacttccgca ttttgctgat tcatatgatc aatattttgg      360
tctccagcag gcacgactga tgttacccca ggcaagtcct tgttcttctc acacactata      420
tttatttatg tccttcaccc attgatattg caccttaacc tcattactgt tcacacccac      480
ctaattgtga gatactgatg aaactcacta acctgactaa tccaaattaa cgcatattta      540
tattatcgtc atgataacta cgttcatgta gaaattatca tctagaatat catcttgcaa      600
cataaactaa actctaaact gtggtcagct gcctacaaca gcttgtttca tcacctcaat      660
ttattgcacg ttcttccaag aaatcttttg acaattcatt gtattgaaat acaggataag      720
ggagtggaac agctgaactg cagtaaaccg aacagn                                756
```

<210> SEQ ID NO 23
<211> LENGTH: 481
<212> TYPE: DNA
<213> ORGANISM: Capsicum annuum

<400> SEQUENCE: 23

```
ggtgtcaaag aggcacctct tgtccattt gttgtatccc ccgacacagc atgagtagaa        60
gttacttcct gatctccgtt ctcaccttgt ggtgcagcat ttagatccac atttagcacg      120
gtatttcttc tcgagttgga ccttgtacgc ttattttgtt gtgcccttct atctcgggta      180
ctcatgttat gctcagttgt accctaatta aaacaggaaa agacggaaaa atttgaagtc      240
atgatagggt ttatattctt aataatctat tacctcaaaa agcaagaata aaagaagta       300
gtagtaatgc aagtatctca aatttactaa atatacttcc gcatgagcta ttacagtgga      360
ccttaacata caccacggcg atcaatgaat agacttgcaa attgtatgtt ttcaagaatt      420
ttagcaagtt gtatttacat tgggctgcga tctggaaagc aaagcatgga catcggaagt      480
g                                                                      481
```

<210> SEQ ID NO 24
<211> LENGTH: 554
<212> TYPE: DNA
<213> ORGANISM: Capsicum annuum
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t

<400> SEQUENCE: 24

```
ggtgttttat gctgccgtat ttggttgtcg cttgtctatt cttttgctgg tgatggtgca    60
ttgcattcaa ttgccatttg catttgtggt gataactttg atactcaaca agccttctct   120
ttgacgtatg ggtttatgga gaactaaaaa aagntagttc ggtgcatgaa gcttcctgca   180
ttcacgcata gtccnagtag ggtcgcaaac tgagggntgt aatgtaggca gcctactcta   240
acaagcatca gcggttaatt ccacggcttg aaccatggag acaactttat cgttgtttca   300
aggctcctcc tctctttcgg agaaaccaga tttgctatac gtgtgtcgtt gttattgtat   360
tagcgcctct tgcaacttcg ataatgtagc atcctcagct agattagatc tgctaccaaa   420
gtccctcctg atacatcttg ctattggact atttagtaca agtatctant gcatcttcat   480
ttaaaaagtt aagaaatcta taaagaaag caagaaggtg aaaattcatt gtagtttcga   540
ctgtctcaaa ctca                                                     554
```

<210> SEQ ID NO 25
<211> LENGTH: 1216
<212> TYPE: DNA
<213> ORGANISM: Capsicum annuum

<400> SEQUENCE: 25

```
gacaaagacc acaagaaagc tctactcatc ttatcttttg ctcttcttgc aatccttttc    60
catcatcctt gtatattctg attcaccatt ttgatcttca atcaattcat aataacatcc   120
aggcactcct tagagaattc acggagaaaa tatcgatggt atagagtttc agattgagta   180
ccacataata gggagccatc atcatcacta agtccaatat gcttcattct tgccttggtc   240
atgagtcgtt tatgcatggt tatctaacat ataaagctat gcgttggtat attggattta   300
ttccacactc ccctccattc aggccagcaa gagccaatcc ctatttacag atatagccac   360
tcagaatagt atattgtcat tccctttaag ccatccattg tgaacatgcc ctgccacaaa   420
tttagccttt agtccacaaa ttttcttcca gtggcaacat gaataagtag gggcatttaa   480
actttaccaa gacaaaaata gaagtcaatc ctcaacccca gatagctatg gtatagatgt   540
ctacctcaag tagctatggt ttctttctat caacagtgac aaaattaaaa tatacatctc   600
gtaatagagt tactttttag taaggtatat attacaaaaa gtggaagaag tcacgtaaca   660
aactatgatc agttagtgtg ctcaatcgta tactgttgta ccgactagct ctgatacaag   720
gcttttttgt gtcactaatc tagatgcact agaaatacaa taggcagctc ctatcatcat   780
atccagcagc attaggcacc gaagtgccaa acccattgga gacgacaata actatcggca   840
tgaaacattc atggagaacc ctctttttct caatagttct ccccacgtct ctctctctct   900
ctctctttgg tgtgtatgta ataggtactc ttggaaaaag acaagttaac tctaagagaa   960
aggagtcatt caaaacttca aaccagaact tgcagcacac ggggctctcc tattatcctc  1020
```

| | |
|---|---|
| agttaaagaa tgggtatcat caatctcaag tataaaatgc tcagcacata cgacatgtca | 1080 |
| agtatctttg ttttggtcga cctgaacact atattattaa actccctagg gaaagagcca | 1140 |
| atcttttgta caactcaaag cagcaagtaa aaaataagta atctacacct atcgactatc | 1200 |
| cttctagcta ttcctc | 1216 |

<210> SEQ ID NO 26
<211> LENGTH: 893
<212> TYPE: DNA
<213> ORGANISM: Capsicum annuum

<400> SEQUENCE: 26

| | |
|---|---|
| gaactcctct tgtgattaaa tcttctagct atgatctgtc tttacacgtt ggctccttca | 60 |
| tgagctctct agtatgcaag catttgtttc cattttaatt ctttggttca ctatctgtgg | 120 |
| gcatgggaca ttgtgattca atagggcctc attctttgcc atccaaatgt ggtatattag | 180 |
| cgctgcggct tctgctcata tgggttccct gctaacccat ccatttgttc gtctcactat | 240 |
| cctagttcag aacccctcga tggttttatt ttttatcctt attttagca attggaggtt | 300 |
| ctcttctaag ctagcttttg aaaaaccgct ctcgaaagat aaagatcatt agtttcattc | 360 |
| tcccttccac atagtaggca gacttcgtct tggcatatcc ccattcagta taatcgatct | 420 |
| cttgttaata gtctcccctg tgcatagtta acaacaaat gaggctgtgc tttggaacat | 480 |
| ttactctatt ccatacacct ctccaagtgg tccataggcc tccttctccc tttgtccaag | 540 |
| tgcagcaact tctgattgtg tatttgcctg aacttgtgag ccagccattg tgtacatagc | 600 |
| ctggagcaaa cactgttttc actctgcaaa tcatttccca gtaccagcag atattaatgg | 660 |
| agggtctata ttcccaccag ttgtcaccct ttaagtaaag tggttcaccc atgtaaccca | 720 |
| aaggttatca gcttttcttg ctttgttcca tacttatttc gctactgctg cttcattcca | 780 |
| agatacagtc tctcaccct aaacttccgt cttttctttgt tctacaaatc atatcccaat | 840 |
| atatatagga ggtagttagc ctgtgttaac atttccactc catataaagt tcc | 893 |

<210> SEQ ID NO 27
<211> LENGTH: 1622
<212> TYPE: DNA
<213> ORGANISM: Capsicum annuum

<400> SEQUENCE: 27

| | |
|---|---|
| cgttgataaa cactagaaga gaatatgtga atggttcatg cacataaaat agattttaca | 60 |
| tatgaagttg tcctcattat ttgtatttgt gatgatgcag acatgtctg aagaaaacta | 120 |
| tacaatcatg ttaatctcag tggttgttat aacaggagtt gtatcacctc ttgttaaggt | 180 |
| tctatatgac ccttcaagta agtacattgc ctacaagagg aggacaataa tgcatagcag | 240 |
| agaaaaagat gaatttcgta tacttgcttg tatacacagc caagaaaatg ttcgcgcagt | 300 |
| catcagttta cttcaagtct cgaatcctac aaaagaaagt tgtattaatc tagtagttct | 360 |
| tcatcttact aagctaacgg gccgtgcctc ctcagttctc atagcccatc aaaagcgtga | 420 |
| caggccatca acaaatccaa cacaatctga agaatcttc aatattttcg aaaaacttga | 480 |
| gcaacaaaac agtgacctca ttatggtaca ttgctacaaa ggagtctcac catatgtaac | 540 |
| aatgcacaat gatgtttgtt cccttgcttt agaaaagaga acaactctta tcattgtccc | 600 |
| ttttcacaag cattggatgt gtgagaaaag aatcgaaaca tcctatgcat atcgacatct | 660 |
| aaacaagaat gtacttgaga aatctccttg ttcagtcggg atactgattg atcgaggcaa | 720 |
| caaaaaaaat ctcgttatgc aatcacagta ccatcattat atagagtcgt ggtactattt | 780 |

```
tttggcggag cagatgatcg cgaagctttg tcatatgcag aaagaatgtc caaacatcct      840
agtgtgaaaa tgacattcat acgtttcacc agatcaggta atgcatttga aaatgttgtt      900
ggtggatcgg agagaagtaa ggttcttgat tcacaaatct tgaatgaatt caatctccaa      960
taccttcatt cagaacaagt ttcttatcaa gaagcagagg tgaaaagagg cgcggacgtg     1020
ttagaagtta ttaaatcttt gggacgtttt tatgatcttg ttatggttgg taaacgtcac     1080
gtagactcac caatattgtt gcaattgaca aagaggactg atgaggatgg tgaattaggg     1140
attgtaggag gcattcttgt cgcctcagat tttgaaagtg agacttcagt tttggtggtg     1200
cagcaacaaa ccagattatg gggacttcat gatcctgaag agtctacaca tttgagaagg     1260
ataaactaat tatagttgta tagacgtatg tcgctctgac tcaatcaaaa atgtcaatgg     1320
atgtgtgtta catcctgaag tagtctacac atttgagaag gataaactaa taattgtagt     1380
tgtatagaca tgttgctctg actcatcaaa aatatcaacg agtacgtgtt agatcttgaa     1440
gagtcttaac acatttgaga aggatcaact tatagttgta tagacctata tcgctcgaac     1500
acttcaaaaa atgttgatgg tgcgtgcaag accttccaaa agaagtgctt ttttcgagaa     1560
tctaacacag gtgctgcact atagtgtcac ctaaatcgta tacgatttag gtgacactat     1620
ag                                                                    1622

<210> SEQ ID NO 28
<211> LENGTH: 393
<212> TYPE: DNA
<213> ORGANISM: Capsicum annuum

<400> SEQUENCE: 28
atcttgttca cttatgagga catctgtcac aggctacatg attaaagttg gtaattcttt       60
ggtctcatga aaagcaaaga agaaaactac attttttaagt agttcagctt aagctgaata     120
cagaagcctt gcttgtactg tgtcagagtt agtatggtta cttagaatac tgaaagaagt      180
agatgctgaa gttcagttac cagttcaagt ttatagtgac aacaaggttg ttattcaaat      240
tgcagtcaat ccagtgttat catgaaagga acaaaccata ttgaaattga ttgtcatttc      300
acaagagaaa aattgcaaca aggcatgatc aaagttaact atcattctac tcaagaacaa      360
ccagttgatg tgttgacaaa aggcttatct aga                                   393

<210> SEQ ID NO 29
<211> LENGTH: 733
<212> TYPE: DNA
<213> ORGANISM: Capsicum annuum

<400> SEQUENCE: 29
gcaagagtta tcacttaaag gaaagaactt gataggcaga aagccaagtt tcacaagcta       60
gattttctgc actaactctg attttgaaat cttgtactac ttttaagtat cgattacaag      120
cacgacatgt tcattagctt cctacttgtt tatcgtaatt atcaaaactt gatttagatg      180
gagtcttggg acagacttta ttgtgataaa aagttgcaga cttttttgtga gagatgtagt     240 tacaatgata gctactgatt gactcgtgaa aaataattga actggatgct ccaatgggac      300
gacctagcca atgatcgagt tggagtatag accttggaac caagattcta attccagtag      360
aggtgataca aagtgaaatt ttcccatcta cctgggcata gttagctgat atcttttctg      420
gtgggaggta acaagtacac ttaagttagt tgaggagtgc gtgaccttcc cgctagctca      480
ggagtgtgca agcttccacg aataccatga tatctttaaa aggaggagtt gatatggtta      540
```

```
caggctcttc caagtcttgc ttcttataca ttttgtacgt gcaaacaagt tgctgaaggg      600
tagatttgat tacaaaaaag ctatttacga caaagatatt gctgtcatgt acttgtacat      660 tgtattctc  tttgttttat tattctttgc tagccgaaca aatttgcttt actctgtgat      720
ttgcagtggt gat                                                         733
```

<210> SEQ ID NO 30
<211> LENGTH: 730
<212> TYPE: DNA
<213> ORGANISM: Capsicum annuum

<400> SEQUENCE: 30

```
gcaaagaact gcagaattta ctcccacact aactgaccat aattacactt caatgtatac       60
atatttgcaa ctttgtcatc atctctacat tctcttttc  cgctacgcca gctggccttt      120
ttataggttt tccaccctaa gatcttggtt tggtaaatgt attttttatt gagcatcgtt      180
tcaaagatta gaatcttaga aaaggaaaag cagccataag ggacgtgaaa tttgggtaac      240
agcttaatta ggctaaacgc ttactacaac aacaacaaca acataccaag tgtaatccca      300
gtattgataa agaaacccag acgataacat aatatgtacc tggaaatgca atcacagta       360 ttgatacacc atcataagat attgacgaac acattatagt atagtacaac tgtgacaaat      420
ttaaacctag taaaatttgt tgtgggaact caaacaattt ggattcaaga agaaaccaag      480
gaactagata atttgtagaa ttttaggac  caaagaaaaa aaaggtgttt ttaaaaaaat      540
catttctttg atttctttga atcttctcct attttccttt tgcttcttct cgagatgctg      600
aagtgatctt ctctgttaaa gtcacaaaat gtgtttaata aaaggttggt gaaatacata      660
tagagctccg taaacttggc aacaattttc acttgaatac ctctacttga ggcttgtacc      720
tattagatac                                                            730
```

<210> SEQ ID NO 31
<211> LENGTH: 430
<212> TYPE: DNA
<213> ORGANISM: Capsicum annuum
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t

<400> SEQUENCE: 31

```
tttattaaca cattttgtga ctttaacaga gaagatcant tcagnatctc cagtagaagc       60
aaaaggaaaa taggagaaga ttcaaagaaa tcaaagaaat gatttttta  aaaacacctt      120 ttttttcttt ggtcctaaaa attctacaaa ttatctagtt ccttggtttc ttcttgaatc      180
caaattgttt gagttcccac aacaaatttt actaggttta aatttgtcac agttgtacta      240
tactataatg tgttcgtcaa tatcttatga tggtgtatca atactgtgat ttgcatttcc      300
aggtacatat tatgttatcg tctgggtttc tttatcaata ctgggattac acttggtatg      360
ttgttgttgt tgttgtagta agcgtttagc ctaattaagc tgttacccaa atttcacgtc      420
ccttatggct                                                            430
```

<210> SEQ ID NO 32
<211> LENGTH: 1887
<212> TYPE: DNA
<213> ORGANISM: Capsicum annuum

<400> SEQUENCE: 32

```
tatagtgcag caggaatact tttgaatcag agaaagtatg tgttggaact tatatctaag    60
ttaggtttga gtgggtcaaa acctgctccc acacctttgg aacttaatca caagctcacc   120
acaatggagt atgatgagat tacagataat actgctggag atgaactatt gagtgatgta   180
agttcatatc aaaagttgat tggaaagttg ttgtatgtta ccatcacaag gcctgatatc   240
agcttctcag tgcaaaccct gagtcagttc atgcagcaac caagaaatc acattgggaa   300
gctgcactca gaactgtaag atacctgaaa aatgcaccag gtcaaggaat ccttatgaaa   360
tctggtcata ctcaacaact acatgttggt gtgactctg actgggcagc atgtccaaac   420
accagaaagt cggttactgg ttttgcagtg aaatttggag agtccttgat ttcttggaat   480
caaagaagca caaaactgtc ttaaggagct cagagtatag aagccttgca gcagcagtag   540
cagagttgac atggttgcaa ggattatttc aggagctgga tgttcacatt gacaaaccta   600
ttgcagtctt cagtgatagt aaatctgcca gattgcagag aatcccatat ttcacgaaag   660
aacaaagcac atcgagatcg attgccattt tatcagagac gagattaaag aaggagtggt   720
taaggctgtc tatgtgaata cgaaggaaca agaagctgac ttgctgacta aggccttgac   780
tacttctcaa cacatgcatt tacttggcaa gcttggagtg ttcaacattt tggaccctcc   840
agcttgaggg ggagtattaa agtcaattag agtcagttag ataggtgctt agctgaagtt   900
agttgcggtt gttagtggta gttgaagttt gttagtagtg aagttgtta gccagctgtc   960
atgtccagct gtcaatgatt aagttagtgg ggcaacaatg agggaagtta ctagaagctt  1020
atgagcttgt gtatatatat tctattccag attgaataat caattaattt cattaccaca  1080
aaatatcttc tttctcaatt cctatcataa actagcaatt ctgtcacttg atgttgcttc  1140
agttttgggt atgggattca ctggatactg gtgttttcga tttgaaatca tctattccat  1200
aatgatgact catagactga tagtacagtc tattggcccc tgttagagtt tatgacccgg  1260
attttgttga tccggccctg aaaagttcac ggtgcgatcc atgtttgtgc tttttgtggg  1320
gtctgtggtg gtgatgtttg tgagcttagg atttatttgt atgcacgtat tatataagtg  1380
catttagtgg gctatttcga gcagttttca catacacgta attgagacta tcgtctccac  1440
cttgtattcc tcttcttcat agtgaatttc ctctctctgc ccgtggtttt tcccatggag  1500
ggtttccacg taaatatgtg tgttcttctt gtttttattt tgcttgtggt attgcctatt  1560
ctgtccgatc ataacaactc caaatatatt tgttcaaaac tggaaggatg gtcgaaggag  1620
tatgagagt ttttcgagcc ttgtgcatac ttagtcgaac gaacttccaa gagatgttct  1680
ttggtgagaa attgttaatt ttcttgaaca cctgaaatga aacaactacg agaaaatgga  1740
ttggcaaaca ctattgtttg acgaattgca tcacgtgttg ctgacagaag acaaaaggat  1800
caatttgata taaatatga ccggtatgtt gggtcctaac aacaacaatt ggattgatct  1860
tttgctaatt gaggagtttc acacgtc                                      1887
```

<210> SEQ ID NO 33
<211> LENGTH: 1024
<212> TYPE: DNA
<213> ORGANISM: Capsicum annuum

<400> SEQUENCE: 33

```
gaactcaata gcccttcttt tattccagct ctaacgggac cttcacattt tctttcgtac    60
aattgcacca ccttctcttc aacagagaaa gaagccagtg ttctgatact tccaactgct   120
```

```
tcactagcaa cttgactcgc atcctygtat agtttctaca agaaaatctt acttaaataa      180
gcactgttag agtgtgtgcc ctactaattt taatatttta ctctactggt ttcctatctg      240
tgcaacaagt cagtaaacgt ggttcacata attaaaagct gaacacagtg tttttaagtg      300
aaaaacaccc ggctcaagaa aggtgtaaag gctcaagaaa agtgtaaaaa accacgacct      360
atacctctac agtatttaaa cccctactta ctataactct gagcctcaa caatcaacaa       420
tattacaaga cttttttgtaa aactaggaat taaaacttcc aactcctata ctacaaaaac    480
acaaatcttc ccaagtcttc gagttcctta acttgaagct cctaactcag tttatagatt     540
actgagacta gaacaatgac tcattacaac tcaaagaacc tatctactac aaacagtcta    600
agactttgct aactaaagga ccaggttctt cttcaagtaa gtgaactgtt ttgctgattg    660
ttgattatct tatcagtgca tgagtgaatg ctttgaaagt tgtttcttcc atttaagcca    720
acacctgatg tatatttcta tcctcactag gactcccagt tagtttcact cattctttac   780
tgccttctct ccctcttgtt gtttgaatag gactcttctt gattatctca taatttctgc    840
aagacttctt attcgaccga acttcttcaa gatttcttat tcaactcaac ttctgcaaga    900
cttcttgttc aaaccaaact tcttcaagat ttcttgttca actcagcttc tgcaagactt    960
cttgttgtga taagtgttat ccactcccat tttgcacgca gattcagttt ttcaataact   1020
tgcc                                                                 1024

<210> SEQ ID NO 34
<211> LENGTH: 782
<212> TYPE: DNA
<213> ORGANISM: Capsicum annuum

<400> SEQUENCE: 34
cacaatgctt agcagttccg ctgtttctct ctaattgtat ccgttcaaaa atacaagctt       60
gtgacagatg aatcttagac tctctgacta cttgtaattc tatctacaat ttagccatct     120
ttctctatca tttgcttttg aaatggagtg acatgaacaa tgaggattca ttcattcagt    180
cgatctccac ttgctttgca ttgaggagtt ttttctctat catttgcttg agagttcaag   240
tgtctgggat ggacaatgtg gtcgttaaca ttgcctcttc tcatccaggt tgttctcttt    300
gcttcttaac tgaggggtat ttcttggttc cggagaatct ttttttttggt aactaacata   360
ttcatttttat taccaaagta atattacaaa tcaactacca gcctgatgac acaacctggt   420
agactcaaag aagaaccta ctgatcagac taataataat gaggatagta gtttagatca    480
ttgatcacag ctgctaactt atgcctaaca gtagcaatac aaataacatc ctgaaatact    540
agcctaacca ctttctccgg tgtagtactg attgtcctga caatcctaca attcctatca    600
tgccatatat ggtaaacgca tgcagcagta ccatcctgaa tatgtgttga ggctgatcga    660
cctttgacat tgttctcaat ccactcaagt tcactggacc aagccaaagc aatcctttga    720
atctttatcc agccgagcaa agcattccca cagtttagca gcatagctac acctaaagaa    780
ct                                                                    782

<210> SEQ ID NO 35
<211> LENGTH: 1641
<212> TYPE: DNA
<213> ORGANISM: Capsicum baccatum

<400> SEQUENCE: 35
gaaatttgtt cttcttcttt cccttccttt tttgttttgg atttttcctca ttgcaagtag     60
aaatgtctct aacggctatg gttttaatag ttcatccgag aagagagtta ctgctgttgc   120
```
catcagtaat gacggtcgtt ttgtagcttt cgcggataaa tttggtgtaa tttatgcagt 180
tgaaatagaa ggttatcatg aaaatcaaac tctgcccgat aagaaggcag tcccgattct 240
tgcccactat tgcagcatca ttactagtct ggtatgtttc tttcctttcc tcttcatgtg 300
aatttgcttt agttttcgat gagtcaattt ttgtatccta tatatatgag ggttagcggt 360
ttactcagat attgttacga tactcatgat ctatgttgct cgaactcttt aaaaatgcta 420
ttaggtgcat gtcggattct tcaaaagtag ggcatttttg gaggatccga cacgagtatg 480
gcaacatttt tggtgagtcg gagcaactta gctcatgatt ggtccttgta agcagttttc 540
tacggaaatt gtgttttcat atacactgtt ctggcaatgg cattcatcgc tcgactcttc 600
tacacaaata ttatggataa tgatctactg tctcgatgca catctcttgc acaatttgtt 660
gcaagcgttg tccatcctgc cagtcaagta taaagcgtta tctttctggt gactagacca 720
tgatactctt atcgtctatg attacttcat ataagattaa gtttagcgta ttcctagctc 780
gccatatcac ataacacttt ctctaccaaa ttagtttgat tccataatca aggcctcttg 840
tttcaaaagc tagttagttt ttgctcaaat aggattttcc atcttgcagg agttttcacc 900
tgacggacga tacgttatta gtgccgatcg agacttcaaa atccgagtaa tgtcatgctt 960
cttattaacc atgaatctta gtaagatttc ttgatgacct ccagctaaca tcaagatttc 1020
ttatgggtca taattacagg tctctgtgtt cccagaaaag ccatcagatg gagctcacga 1080
gattcaaagc ttttgccttg gccatacaga gtaagaattt cttgaaactt gggtggtccg 1140
aactccgaat accctcagtt ttgataatca agctgatcca gaatagtcgt tttctgttga 1200
aatgttggtt atactgctaa aattgttaaa atctagtgac agtttcttgt cattatcggt 1260
aaaagccaat cttgacattt gaccaggata agtcgaccag gacgatttag gttgtcattt 1320
tttgtgtcgt ccgacttgta catctgatta aattatctat accatgcaga aacagtgtcg 1380
ctggagcatt tttatgtgta ttttccgaat ttattctcct tttacacgtt ttataggtta 1440
gggaatctgg gtggtgcgga agtagacaat aacgaaagca aataaacagt gactaacgca 1500
aataaagaag acacaaattt tacgtggttc tattagttag acataatcct tgcgtgggag 1560
tggggggtgg ggatgtgcta ctgttagctg tgtttctacg tcggtaccct tgttgactta 1620
tctttttttg gatataaaaa a 1641

<210> SEQ ID NO 36
<211> LENGTH: 782
<212> TYPE: DNA
<213> ORGANISM: Capsicum baccatum

<400> SEQUENCE: 36
cacaatgctt agcagttccg ctgtttctct ctaattgtat ccgttcaaaa atacaagctt 60
gtgacagatg aatcttagac tctctgacta cttgtaattc tatctacaat ttagccatct 120
ttctctatca tttgcttttg aaatggagtg acatgaacaa tgaggattca ttcattcagt 180
cgatctccac ttgctttgca ttgaggagtt ttttctctat catttgcttg agagttcaag 240
tgtctgggat ggacaatgtg gtcgttaaca ttgcctcttc tcatgcaggt ttgttctttt 300
gcttcttaac tgaggggtat ttcttggttc cggagaatct tttttttggt aactaacata 360
ttcattttat taccaaagta atattacaaa tcaactacca gcctgatgac acaacctggt 420
agactcaaag aagaacccta ctgatcagac taataataat gaggatagta gtttagatca 480
ttgatcacag ctgctaactt atgcctaaca gtagcaatac aaataacatc ctgaaatact 540

```
agcctaacca ctttctccgg tgtagtactg attgtcctga caatcctaca attcctatca    600
tgccatatat ggtaaacgca tgcagcagta ccatcctgaa tatgtgttga ggctgatcga    660
cctttgacat tgttctcaat ccactcaagt tcactggacc aagccaaagc aatcctttga    720
atctttatcc agccgagcaa agcattccca cagtttagca gcatagctac acctaaagaa    780
ct                                                                   782
```